United States Patent
Sakurai et al.

(10) Patent No.: US 9,737,868 B2
(45) Date of Patent: Aug. 22, 2017

(54) REFORMING DEVICE AND REFORMING METHOD, AND DEVICE FOR MANUFACTURING CHEMICAL PRODUCTS EQUIPPED WITH REFORMING DEVICE AND METHOD FOR MANUFACTURING CHEMICAL PRODUCTS

(71) Applicant: MITSUBISHI HEAVY INDUSTRIES, LTD., Tokyo (JP)

(72) Inventors: Mikiya Sakurai, Tokyo (JP); Naoya Okuzumi, Tokyo (JP); Ryota Shimura, Tokyo (JP); Shuichi Miyamoto, Tokyo (JP); Yoshio Seiki, Tokyo (JP); Hiroyuki Osora, Tokyo (JP)

(73) Assignee: MITSUBISHI HEAVY INDUSTRIES, LTD., Tokyo (JP)

( * ) Notice: Subject to any disclaimer, the term of this patent is extended or adjusted under 35 U.S.C. 154(b) by 121 days.

(21) Appl. No.: 14/423,637

(22) PCT Filed: Sep. 3, 2013

(86) PCT No.: PCT/JP2013/073705
§ 371 (c)(1),
(2) Date: Feb. 24, 2015

(87) PCT Pub. No.: WO2014/042042
PCT Pub. Date: Mar. 20, 2014

(65) Prior Publication Data
US 2015/0202589 A1  Jul. 23, 2015

(30) Foreign Application Priority Data
Sep. 12, 2012 (WO) .................. PCT/JP2012/073374

(51) Int. Cl.
*B01J 7/00* (2006.01)
*B01J 19/24* (2006.01)
(Continued)

(52) U.S. Cl.
CPC ............ *B01J 19/245* (2013.01); *B01D 53/48* (2013.01); *C01B 3/323* (2013.01); *C01B 3/384* (2013.01);
(Continued)

(58) Field of Classification Search
CPC combination set(s) only.
See application file for complete search history.

(56) References Cited

U.S. PATENT DOCUMENTS 6,100,303 A    8/2000 Hirotani et al.
7,037,485 B1   5/2006 Drnevich et al.
(Continued)

FOREIGN PATENT DOCUMENTS

CN   101980952 A   2/2011
EP      1016643 A1  7/2000
(Continued)

OTHER PUBLICATIONS

Translation of the Written Opinion (Form PCT/ISA/237) mailed Oct. 8, 2013, issued in corresponding International Application No. PCT/JP2013/073705 (5 pages).
(Continued)

*Primary Examiner* — Imran Akram
(74) *Attorney, Agent, or Firm* — Westerman, Hattori, Daniels & Adrian, LLP

(57) ABSTRACT

A reforming device according to the present invention has a compressor, a first heat exchanger, a desulfurization device, a reformer, a raw material gas branching line that extracts a compressed natural gas from a downstream side of the desulfurization device with respect to the flow direction of the natural gas and supplies the natural gas to the reformer, and a flue gas discharging line that discharges a flue gas generated in the reformer, wherein the first heat exchanger
(Continued)

is provided in the flue gas discharging line, and the flue gas is used as a heating medium of the compressed natural gas.

7 Claims, 19 Drawing Sheets

(51) Int. Cl.
    *C01B 31/18* (2006.01)
    *C01B 31/20* (2006.01)
    *C01B 3/38* (2006.01)
    *C01C 1/04* (2006.01)
    *B01D 53/48* (2006.01)
    *C01B 3/32* (2006.01)
    *C07C 29/151* (2006.01)
    *C07C 273/10* (2006.01)

(52) U.S. Cl.
    CPC .............. *C01B 31/18* (2013.01); *C01B 31/20* (2013.01); *C01C 1/04* (2013.01); *C01C 1/0488* (2013.01); *C07C 29/1518* (2013.01); *C07C 273/10* (2013.01); *B01J 2219/00087* (2013.01); *B01J 2219/24* (2013.01); *C01B 2203/0233* (2013.01); *C01B 2203/0475* (2013.01); *C01B 2203/061* (2013.01); *C01B 2203/068* (2013.01); *C01B 2203/0811* (2013.01); *C01B 2203/0816* (2013.01); *C01B 2203/0833* (2013.01); *C01B 2203/1258* (2013.01); *Y02P 20/129* (2015.11); *Y02P 20/52* (2015.11)

(56) References Cited

U.S. PATENT DOCUMENTS

| | | | |
|---|---|---|---|
| 2002/0024038 A1 | 2/2002 | Iijima et al. | |
| 2006/0143983 A1* | 7/2006 | Matsui | B01J 8/0285 48/61 |
| 2009/0305093 A1* | 12/2009 | Biollaz | B01J 12/007 429/426 |
| 2011/0175032 A1* | 7/2011 | Gunther | B01D 53/1462 252/373 |

FOREIGN PATENT DOCUMENTS

| | | |
|---|---|---|
| JP | 6-234517 A | 8/1994 |
| JP | 11-263740 A | 9/1999 |
| JP | 2000-63115 A | 2/2000 |
| JP | 2000-169411 A | 6/2000 |
| JP | 2001-122812 A | 5/2001 |
| RU | 2203214 C1 | 4/2003 |
| RU | 2258691 C1 | 8/2005 |
| SU | 579220 A1 | 11/1977 |

OTHER PUBLICATIONS

Chinese Office Action dated Dec. 1, 2015, issued in counterpart Chinese Patent Application No. 201380044698.0, with English translation. (12 pages).
International Search Report dated Oct. 8, 2013 issued in corresponding application No. PCT/JP2013/073705.
Written Opinion of the International Searching Authority dated Oct. 8, 2013 issued in corresponding application No. PCT/JP2013/073705.
Office Action dated May 31, 2016, issued in counterpart Russian Patent Application No. 2015106410, with English translation. (8 pages).
Extended (Supplementary) European Search Report dated Jun. 1, 2016, issued in counterpart European Patent Application No. 13837204.0. (10 pages).
Notice of Allowance dated Nov. 24, 2015 issued in counterpart Japanese patent application No. 2014-535496, with English translation. (3 pages).
Notification of Grant of Invention Patent dated Aug. 5, 2016, issued in counterpart Chinese Patent Application No. 201380044698.0, with English translation. (2 pages).
Notification of Completion of Formalities for Registration dated Aug. 5, 2016, issued in counterpart Chinese Patent Application No. 201380044698.0, with English translation. (2 pages).
Official Decision of Grant dated Sep. 6, 2016, issued in counterpart Russian Patent Application No. 2015106410, with English translation. (17 pages).

* cited by examiner

REFORMING DEVICE AND REFORMING METHOD, AND DEVICE FOR MANUFACTURING CHEMICAL PRODUCTS EQUIPPED WITH REFORMING DEVICE AND METHOD FOR MANUFACTURING CHEMICAL PRODUCTS

FIELD

The present invention relates to a reforming device that reforms a natural gas by using the natural gas as a fuel of a reformer for reforming the natural gas or the like, and a device for manufacturing chemical products equipped with the same.

BACKGROUND

When manufacturing methanol and ammonia, a reformed gas obtained by reforming the natural gas or the like in the reformer is used (for example, see Patent Literatures 1 and 2). When the natural gas or the like is reformed in the reformer to convert the natural gas to the reformed gas, before supplying the natural gas to the reformer, a part of the natural gas is extracted and used as fuel of the reformer, and the natural gas supplied to the reformer is reformed.

CITATION LIST

Patent Literature

Patent Literature 1: Japanese Laid-open Patent Publication No. 6-234517
Patent Literature 2: Japanese Laid-open Patent Publication No. 2000-63115 (Japanese Patent No. 4168210)

SUMMARY

Technical Problem

As in Patent Literatures 1 and 2, in the method for manufacturing methanol and ammonia which have been conventionally used, in general, the natural gas is first compressed to a reforming pressure. Moreover, a part of the natural gas which has not been desulfurized is extracted before compressing the natural gas and is used as fuel of the reformer. Thereafter, for improving production efficiency of methanol and ammonia, in order to improve a quantity of heat recovery from the reformer flue gas and improve the thermal efficiency when reforming the natural gas, there is a need to further improve the reforming device.

The present invention has been made in view of the above-described problems, and an object thereof is to provide a reforming device and a reforming method capable of improving the thermal efficiency when reforming the natural gas, a manufacturing device of chemical products equipped with the reforming device, and a method for manufacturing chemical products.

Solution to Problem

According to a first aspect of the present invention in order to solve the above-mentioned problems, there is provided a reforming device including: a first compression unit that compresses a raw material gas containing hydrocarbon and sulfur; a first heat-exchange unit that heats the compressed raw material gas; a desulfurization unit that removes sulfur content contained in the heated raw material gas; a reforming unit that reforms the hydrocarbon in the raw material gas to either one or both of $H_2$ and CO or $H_2$ and $CO_2$ to generate a reformed gas containing either one or both of $H_2$ and CO or $H_2$ and $CO_2$; a raw material gas branching line that extracts a part of the compressed raw material gas from either one or both of an upstream side and a downstream side of the desulfurization unit with respect to a flow direction of the raw material gas, and supplies the part of the compressed raw material gas as a combustion fuel used for heating in the reforming unit; a flue gas discharging line that discharges a flue gas, which is generated by combustion in the reforming unit, from the reforming unit; and a second heat-exchange unit that heat-exchanges the combustion air used for heating in the reforming unit with the flue gas which is heat-exchanged in the first heat exchange unit, wherein the first heat exchange unit is provided in the flue gas discharging line, and the flue gas is used as a heating medium of the compressed raw material gas, and the second heat exchange unit is provided on the downstream side of the first heat exchange unit of the flue gas discharging line, and is used as the heating medium of the combustion air by residual heat which is heat-exchanged in the first heat exchange unit.

According to a second aspect of the present invention, there is provided the reforming device according to the first aspect, wherein the reforming unit has a first reforming unit that supplies vapor to the raw material gas to primarily reform the hydrocarbon in the raw material gas to either one or both of $H_2$ and CO or $H_2$ and $CO_2$, and a second reforming unit that secondarily reforms the hydrocarbon in the raw material gas after the primary reforming in the first reforming unit to either one or both of $H_2$ and CO or $H_2$ and $CO_2$ to be a reformed gas, using the combustion air and the compressed raw material gas supplied from the raw material gas branching line.

According to a third aspect of the present invention, there is provided the reforming device according to the first or second aspect, wherein a third heat exchanger configured to heat-exchange feed water supplied to a steam generation unit with the flue gas is provided between the first heat exchange unit and the second heat exchange unit.

According to a fourth aspect of the present invention, there is provided the reforming device according to the third aspect, further including: a fourth heat exchanger that is provided in the raw material gas branching line to heat-exchange the compressed raw material gas before being introduced into the first heat exchanger with a part of the branched raw material gas.

According to a fifth aspect of the present invention, there is provided the reforming device according to any one of the first to fourth aspects, including any one or both of: a denitrification unit that is provided between the reforming unit of the flue gas discharging line and the heat exchange unit to remove NOx contained in the flue gas that is generated in the reforming unit; and a $CO_2$ recovery unit that is provided on the downstream side of the heat exchange unit with respect to the flow direction of the flue gas of the flue gas discharging line to remove $CO_2$ contained in the flue gas.

According to a sixth aspect of the present invention, there is provided a device for manufacturing chemical products including: the reforming device according to any one of the first to fifth aspects; and a chemical product generation unit that manufactures chemical products using the reformed gas.

According to a seventh aspect of the present invention, there is provided the device for manufacturing chemical products according to the sixth aspect, wherein the chemical product generation unit is an ammonia synthesis unit that synthesizes ammonia using the reformed gas which has been reformed.

According to an eighth aspect of the present invention, there is provided the device for manufacturing chemical products according to the seventh aspect, wherein the chemical product generation unit is a urea synthesis unit that synthesizes urea using the obtained ammonia.

According to a ninth aspect of the present invention, there is provided the device for manufacturing chemical products according to the sixth aspect, wherein the chemical product generation unit is a methanol synthesis unit that synthesizes methanol using the reformed gas which has been reformed.

According to a tenth aspect of the present invention, there is provided a reforming method including: a first heat-exchange step of heating a raw material gas containing compressed hydrocarbon and sulfur; a desulfurization step of removing sulfur content contained in the heated raw material gas; a reforming step of reforming the hydrocarbon in the raw material gas to either one or both of $H_2$ and CO or $H_2$ and $CO_2$ to generate a reformed gas containing either one or both of $H_2$ and CO or $H_2$ and $CO_2$; and a second heat-exchange step of heat-exchanging a combustion air used for heating in the reforming step with the flue gas that is heat-exchanged in the first heat-exchange step, wherein the compressed raw material gas is extracted from either one or both of an upstream side and a downstream side of the desulfurization step with respect to a flow direction of the raw material gas, and is supplied as a combustion fuel used for heating in the reforming step, and the flue gas generated by combustion in the reforming step is discharged from the reforming step, the flue gas is subjected to a first heat-exchange by being used as a heating medium of the compressed raw material gas, and the flue gas of residual heat after heat-exchange of the compressed raw material gas is subjected to a second heat-exchange as a heating medium of the combustion air.

According to an eleventh aspect of the present invention, there is provided the reforming method according to the tenth aspect, wherein a third heat-exchange step of heat-exchanging feed water supplied to a steam generation unit with the flue gas is provided between the first heat-exchange step and the second heat-exchange step.

According to a twelfth aspect of the present invention, there is provided the reforming method according to the eleventh aspect, further including: a fourth heat-exchange step that is provided in the raw material gas branching line to heat-exchange the compressed raw material gas introduced into the first heat-exchange step with a part of the branched raw material gas.

According to a thirteenth aspect of the present invention, there is provided a method for manufacturing chemical products including: the reforming step according to any one of the tenth to eleventh aspects; and a chemical product generation step of manufacturing chemical products using the reformed gas.

According to a fourteenth aspect of the present invention, there is provided the method for manufacturing chemical products according to the thirteenth aspect, wherein the chemical product generation step is an ammonia synthesizing step of synthesizing ammonia using the reformed gas which has been reformed.

According to a fifteenth aspect of the present invention, there is provided the method for manufacturing chemical products according to the fourteenth aspect, wherein the chemical product generation step is a urea synthesizing step of synthesizing urea using the obtained ammonia.

According to a sixteenth aspect of the present invention, there is provided the method for manufacturing chemical products according to the thirteenth aspect, wherein the chemical product generation step is a methanol synthesizing step of synthesizing methanol using the reformed gas which has been reformed.

Advantageous Effects of Invention

According to the present invention, since it is possible to improve the quantity of heat recovery from the heat medium to the natural gas when heating the natural gas, it is possible to improve the thermal efficiency when reforming the natural gas.

DESCRIPTION OF EMBODIMENTS

Figure 1:
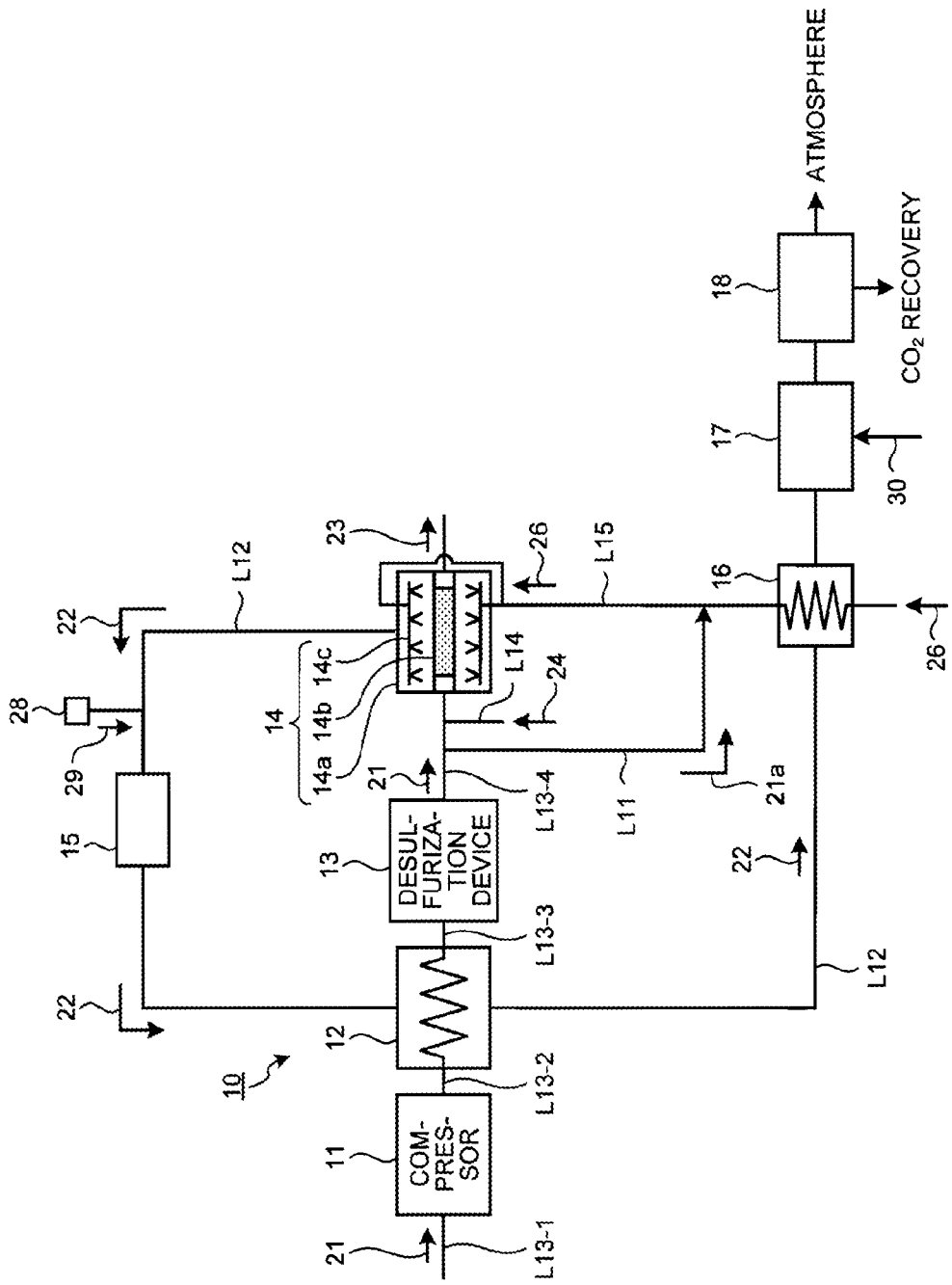
FIG. 1 is a schematic diagram of a reforming device according to a first embodiment of the present invention.

The present invention will be described in detail below while referring to the drawings. The present invention is not intended to be limited by modes for carrying out the invention (hereinafter, referred to as embodiments) described below. In addition, constituent elements in the embodiments described below include elements that can be easily assumed by those skilled in the art, substantially identical elements, and elements of the so-called equivalent range. Furthermore, the constituent elements disclosed in the embodiments described below can be suitably combined with one another.

First Embodiment

<Reforming Device>

A reforming device according to a first embodiment of the present invention will be described with reference to the drawings. FIG. 1 is a schematic diagram of a reforming device according to the first embodiment of the present invention. As illustrated in FIG. 1, a reforming device 10 has a compressor (compression unit) 11, a first heat exchanger (heat exchange unit) 12, a desulfurization device (desulfurization unit) 13, a reformer (reforming unit) 14, a denitrification device (denitrification unit) 15, a second heat exchanger 16, a cooling device 17, a $CO_2$ recovery device ($CO_2$ recovery unit) 18, a raw material gas branching line L11, and a flue gas discharging line L12.

In the present embodiment, although a natural gas 21 is used as a raw material gas containing hydrocarbon and sulfur, the raw material gas is not limited thereto, any raw material gas containing hydrocarbon may be used, and for example, a liquefied petroleum gas (LPG), a synthetic gas such as butane or naphtha obtained from other hydrocarbon, a natural gas liquid (NGL) produced due to production of crude oil and natural gas, methane hydrate or the like is adopted.

The compressor 11 is intended to compress the natural gas 21, and raises the natural gas 21 to a predetermined pressure. The natural gas 21 is supplied to the compressor 11 through a raw material gas supply line L13-1. After the natural gas 21 is raised to a predetermined pressure in the compressor 11 to become a high temperature, the natural gas 21 is supplied to the first heat exchanger 12 through the raw material gas supply line L13-2.

The first heat exchanger 12 is intended to heat the compressed natural gas 21. The first heat exchanger 12 is provided in a flue gas discharging line L12. As the first heat exchanger 12, for example, a convection coil type heat exchanger is used. The first heat exchanger 12 circulates flue gas 22 inside the duct by setting a duct side as a secondary side, and a tube (heat transfer tube) side of the first heat exchanger 12 is set to a primary side. Moreover, the first heat exchanger 12 circulates the flue gas 22 discharged from the reformer 14 as a heating medium inside the duct, as described below. The first heat exchanger 12 uses the flue gas 22 to be supplied to the outer circumference of the heat transfer tube as a heat source, and circulates the natural gas 21 inside the heat transfer tube to heat the natural gas 21.

In addition, the first heat exchanger 12 is not limited to a convection coil type heat exchanger, and any heat exchanger which is capable of performing the indirect heat exchange between the natural gas 21 and the flue gas 22 may be used.

After the natural gas 21 is heated by being heat-exchanged with the flue gas 22 in the first heat exchanger 12, the natural gas 21 is supplied to the desulfurization device 13 through the raw material gas supply line L13-3.

The desulfurization device 13 is intended to remove the sulfur content (S content), such as hydrogen sulfide ($H_2S$) contained in the heated natural gas 21, and organosulfur compound. A conventionally known device is used as the desulfurization device 13, and either wet type or dry type can be used. When the desulfurization device 13 is an absorber that removes the S content in the natural gas 21 in a wet process, in the desulfurization device 13, for example, lime slurry (an aqueous solution prepared by dissolving limestone powder in water) is used as an alkaline absorbent, and the internal temperature of the absorber is adjusted to about 30° C. to 80° C. The lime slurry is supplied to the absorber bottom of the desulfurization device 13. The lime slurry supplied to the absorber bottom of the desulfurization device 13 is sent to a plurality of nozzles in the desulfurization device 13 via an absorbent feed line or the like, and is ejected, for example, toward an absorber top side of the absorber from the nozzle. When the natural gas 21 rising from the absorber bottom side of the desulfurization device 13 comes into gas-liquid contact with the lime slurry ejected from the nozzle, the S content in the natural gas 21 is absorbed by the lime slurry and is separated and removed from the natural gas 21. Inside the desulfurization device 13, the S content in the natural gas 21 generates a reaction with the lime slurry represented by the following formula (1). Furthermore, the lime slurry, which has absorbed the S content in the natural gas 21, is oxidized by air (not illustrated) supplied to the absorber bottom of the desulfurization device 13, and generates the reaction with air represented by the following formula (2). In this way, the S content in the natural gas 21 is captured in the form of gypsum $CaSO_4 \cdot 2H_2O$ in the desulfurization device 13.

$$CaCO_3+SO_2+0.5H_2O \rightarrow CaSO_3 \cdot 0.5H_2O+CO_2 \qquad (1)$$

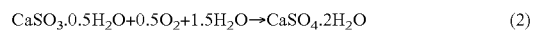

$$CaSO_3 \cdot 0.5H_2O+0.5O_2+1.5H_2O \rightarrow CaSO_4 \cdot 2H_2O \qquad (2)$$

The natural gas 21 purified by the lime slurry is discharged from the absorber top side of the desulfurization device 13. Thereafter, the natural gas 21 is supplied into the reformer 14 through the raw material gas supply line L13-4. The raw material gas supply line L13-4 is connected to a vapor supply line L14. A vapor 24 is supplied into the raw material gas supply line L13-4 through the vapor supply line L14, and is mixed with the natural gas 21. After the natural gas 21 is mixed with the vapor 24 in the vapor supply line L14, the mixture is supplied into the reformer 14.

The reformer 14 is intended to reform hydrocarbon in the natural gas 21 to either one or both of $H_2$ and CO or $H_2$ and $CO_2$, and generate a reformed gas 23 containing either one or both of $H_2$ and CO or $H_2$ and $CO_2$. The reformer 14 has a main body 14a, a catalyst reaction tube 14b, and a burner 14c. The catalyst reaction tube 14b is provided inside the main body 14a, and a reforming catalyst layer having a reforming catalyst is provided inside the catalyst reaction tube 14b. The burner 14c is provided inside the main body 14a, and heats the catalyst reaction tube 14b, by combusting a combustion air 26 to generate a flue gas 22. The burner 14c is connected to the air supply line L15. The combustion air 26 is supplied to the burner 14c through the air supply line L15. As will be described below, after the combustion air 26 is heated by being heat-exchanged with the flue gas 22 in the second heat exchanger 16, the combustion air 26 is supplied to the reformer 14. The catalyst reaction tube 14b is heated by the flue gas 22, the natural gas 21 comes into contact with the reforming catalyst when passing through the reforming catalyst layer of the catalyst reaction tube 14b, and thus, as in the following formulas (3) and (4), hydrocarbon in the natural gas 21 is reformed to $H_2$ and CO or $H_2$ and $CO_2$. Thus, a reformed gas 23 containing either one or both of $H_2$ and CO or $H_2$ and $CO_2$ is produced. The gas temperature of the reformed gas 23 is in the range of, for example, 400° C. to 1000° C.

$$CH_4 + H_2O \rightarrow CO + 3H_2 \tag{3}$$

$$CH_4 + 2H_2O \rightarrow CO_2 + 4H_2 \tag{4}$$

The raw material gas branching line L11 connects a downstream side of the desulfurization device 13 with the air supply line L15. The raw material gas branching line L11 extracts a part of the natural gas 21 compressed by the compressor 11 from the downstream side of the desulfurization device 13 with respect to the flow direction of the natural gas 21 as a branch gas 21a, and mixes the branch gas 21a with the flue gas 22 passing through the air supply line L15. In regard to the branched branch gas 21a, since the S content contained in the natural gas 21 is removed by the desulfurization device 13, the natural gas 21 containing no S content is supplied to the air supply line L15.

The reformed gas 23 produced in the reformer 14 is used as a raw material gas for synthesizing hydrogen, liquid hydrocarbon, methanol, ammonia or the like. Also, the flue gas 22 discharged from the reformer 14 is supplied to a denitrification device 15 through the flue gas discharging line L12.

The flue gas discharging line L12 is a line for discharging the flue gas 22 which is generated by combusting the fuel containing the natural gas 21 extracted to the raw material gas branching line L11 as a fuel, using the combustion air 26 in the reformer 14. In the middle of the flue gas discharging line L12, the denitrification device 15, and a reducing agent injector 28 located on the upstream side of the denitrification device 15 are provided. On the way in which the flue gas 22 passing through the flue gas discharging line L12 is supplied to the denitrification device 15, a reducing agent 29 is supplied to the flue gas 22 from the reducing agent injector 28. As the reducing agent 29, for example, ammonia ($NH_3$), urea ($NH_2(CO)NH_2$), ammonium chloride ($NH_4Cl$) and the like are used. The reducing agent 29 is supplied to the flue gas discharging line L12 as a solution or gas containing the reducing agent 29. When a solution containing the reducing agent 29 is supplied to the flue gas discharging line L12, droplets of the solution containing the reducing agent 29 are vaporized by evaporation by high-temperature ambient temperature of the flue gas 22.

The flue gas 22 is supplied to the denitrification device 15 through the flue gas discharging line L12 in a state of containing the reducing agent 29.

The denitrification device 15 is provided between the reformer 14 of the flue gas discharging line L12 and the first heat exchanger 12 to remove the nitrogen oxides (NOx) contained in the flue gas 22 generated in the reformer 14. As the denitrification device 15, a conventionally known device is used, and for example, as the denitrification device 15, a device equipped with a denitrification catalyst layer in which a denitrification catalyst for removing NOx in the flue gas 22 is filled is used. When the flue gas 22 supplied into the denitrification device 15 comes into contact with the denitrification catalyst filled in the denitrification catalyst layer, the reduction reaction of NOx in the flue gas 22 on the denitrification catalyst with the reducing agent 29 progresses as in the following formula (5) and NOx is reduced, and NOx is decomposed and removed into nitrogen gas ($N_2$) and water ($H_2O$).

$$4NO + 4NH_3 + O_2 \rightarrow 4N_2 + 6H_2O \tag{5}$$

After NOx in the flue gas 22 is removed by the denitrification device 15, the flue gas 22 is supplied to the first heat exchanger 12. Moreover, in the first heat exchanger 12, as described above, the flue gas 22 is heat-exchanged with the natural gas 21 to heat the natural gas 21. Thereafter, the flue gas 22 is supplied to the second heat exchanger 16 from the first heat exchanger 12 through the flue gas discharging line L12.

The second heat exchanger 16 is intended to heat the combustion air 26. Like the first heat exchanger 12, the second heat exchanger 16 is provided in the flue gas discharging line L12. As the second heat exchanger 16, like the first heat exchanger 12, a convection coil type heat exchanger is used. The second heat exchanger 16 circulates the flue gas 22 inside the duct by setting the duct side as a secondary side, and circulates the combustion air 26 inside the heat transfer tube by setting the tube (heat transfer tube) side as a primary side. The second heat exchanger 16 uses the flue gas 22 supplied to the outside of the heat transfer tube as a heat source, and circulates the combustion air 26 inside the heat transfer tube to heat the combustion air 26.

After the flue gas 22 is heat-exchanged with the combustion air 26 in the second heat exchanger 16, the flue gas 22 is supplied to the cooling device 17. Also, after the combustion air 26 is heated by being heat-exchanged with the flue gas 22 in the second heat exchanger 16, the combustion air 26 is supplied to the reformer 14.

The cooling device 17 is intended to cool the flue gas 22. The cooling device 17 is a cooling tower in which a cooling water 30 is circulated through the interior and the exterior. In the cooling device 17, the cooling water 30 is supplied from the tower top side, and the flue gas 22 supplied into the tower is cooled by being brought into gas-liquid contact with the cooling water 30. After the cooling water 30 comes into gas-liquid contact with the flue gas 22, the cooling water 30 is stored in the tower bottom, extracted to the outside, and cooled by the cooler. Thereafter, the cooling water 30 is supplied into the cooling tower again and is brought into gas-liquid contact with the flue gas 22. The cooling device 17 may be a device that cools the flue gas 22 by the indirect heat-exchange with the cooling water 30, without being limited to a device that cools the flue gas 22 by bringing the flue gas 22 into direct-contact with the cooling water 30.

After the flue gas 22 is cooled by the cooling device 17, the flue gas 22 is supplied to the $CO_2$ recovery device 18.

The $CO_2$ recovery device 18 is intended to remove $CO_2$ contained in the flue gas 22. The $CO_2$ recovery device 18 is provided on the downstream side of the second heat exchanger 16 with respect to the flow direction of the flue gas 22 of the flue gas discharging line L12. As the $CO_2$ recovery device 18, a conventionally known device can be used. As the $CO_2$ recovery device 18, for example, it is possible to use a device equipped with a $CO_2$ absorber that absorbs $CO_2$ of the flue gas 22 in the $CO_2$ absorbent by gas-liquid contact between amine-based $CO_2$ absorbent and the flue gas 22 in the absorber, and a regenerator that regenerates the $CO_2$ absorbent by diffusing $CO_2$ absorbed in the $CO_2$ absorbent within the regenerator. By bringing the flue gas 22 into gas-liquid contact with the $CO_2$ absorbent in the $CO_2$ absorber, $CO_2$ in the flue gas 22 is absorbed by the $CO_2$ absorbent, and $CO_2$ in the flue gas 22 is removed. After $CO_2$ contained in the flue gas 22 is removed by the $CO_2$ recovery device 18, the flue gas 22 is released into the atmosphere as a purified gas.

Also, the raw material gas branching line L11 connects the downstream side of the desulfurization device 13 with the air supply line L15, and mixes the natural gas 21 compressed by the compressor 11 with the flue gas 22 passing through the air supply line L15, by extracting the natural gas 21 from the downstream side of the desulfurization device 13 with respect to the flow direction of the natural gas 21. Since the S content contained in the natural gas 21 is removed by the desulfurization device 13, the natural gas 21 containing no S content can be supplied to the air supply line L15. As a result, the S content is not contained in the flue gas 22 discharged from the reformer 14. As a result, since the S content in the flue gas 22 is a very small amount, an acid dew point temperature itself is lowered. Therefore, since it is possible to further reduce the flue gas temperature and increase the amount of recovery heat from the flue gas, it is possible to reduce the fuel of the reformer 14.

For example, it is possible to reduce the amount of the natural gas 21, which is used as fuel in the reformer 14, for example, to about 0.7% to 8.5%.

That is, in the methods for manufacturing methanol and ammonia which has been conventionally used, as in Patent Literatures 1 and 2, in many cases, in general, a part of the natural gas that has not been desulfurized is extracted and used as a fuel of the reformer. Therefore, when the quantity of heat recovery of the flue gas increases and the temperature of the flue gas drops, there is a possibility that sulfuric acid corrosion occurs due to the S content such as sulfuric anhydride contained in the flue gas in a passage of a piping through which the flue gas passes. The sulfuric acid corrosion refers to a phenomenon in which the temperature of the flue gas becomes the dew point temperature or lower of the acid of the S content such as sulfuric anhydride contained in the flue gas, the S content contained in the flue gas is combined with water, becomes sulfuric acid ($H_2SO_4$) and is condensed, thereby corroding the metal. Therefore, as the material of the piping through which the flue gas passes, it is necessary to use acid-resisting steel having a high corrosion resistance against acids such as sulfuric acid. In contrast, in the present embodiment, since the flue gas 22 discharged from the reformer 14 does not include the S content, even if the flue gas 22 is heat-exchanged with the combustion air 26 in the second heat exchanger 16 and the temperature of the flue gas 22 drops, it is possible to prevent an occurrence of corrosion in the passage of the flue gas discharging line L12 on the downstream side in the gas flow direction of the flue gas 22 from the second heat exchanger 16 of the flue gas discharging line L12. Therefore, as the material of the flue gas discharging line L12, it is possible to use other materials without being limited to the acid-resisting steel, and the application scope can be widened.

Also, in the methods for manufacturing the methanol and ammonia which have been conventionally used as in Patent Literatures 1 and 2, in consideration of the possibility of causing the sulfuric acid corrosion in the passage of the piping through which the flue gas passes, it is not possible to sufficiently perform the recovery of heat which is held by the flue gas in the heat exchanger that heat-exchanges the flue gas and the natural gas. Thus, there is a possibility that operating costs of the plant equipment for manufacturing methanol and ammonia increase, and the manufacturing costs of the product increase. In contrast, in the present embodiment, since it is possible to suppress an occurrence of corrosion in the flue gas discharging line L12 even if the temperature of the flue gas 22 drops in the second heat exchanger 16, it is possible to further cool the flue gas 22. Therefore, it is possible to further recover heat, which is held by the flue gas 22 in the second heat exchanger 16, by the combustion air 26, and it is possible to improve the thermal efficiency of the reforming device 10.

Here, although the heat-exchange in the second heat exchanger 16 is, for example, 175° C. in view of the acid dew point, it can be lowered to the lower limit value of 120° C. In addition, 120° C. of the lower limit value is a flue gas temperature that is determined in consideration of the dew point of water.

Furthermore, when the denitrification device 15 or the like is installed in the flue gas discharging line L12, the reducing agent 29 such as ammonia is supplied to the flue gas duct. However, in the methods for manufacturing methanol and ammonia which have been conventionally used, as in Patent Literatures 1 and 2, there is a possibility that unreacted ammonia (also referred to as leak ammonia) reacts with the S content to precipitate ammonium sulfate, ammonium hydrogen sulfate or the like. The ammonium sulfate may be precipitated in a heat transfer tube or a coil in the heat exchanger which heat-exchanges the flue gas and the natural gas, and may block the interior of the piping through which the flue gas passes, thereby increasing the pressure loss. The ammonium hydrogen sulfate may cause corrosion in the heat exchanger which heat-exchanges the flue gas and the natural gas, and the material which forms the piping through which flue gas passes. In contrast, in the present embodiment, since the S content does not exist in the flue gas 22 discharged from the reformer 14, even if the reducing agent 29 such as ammonia is supplied to the flue gas discharging line L12 on the upstream side of the denitrification device 15, it is possible to suppress ammonium sulfate, ammonium hydrogen sulfate or the like from being produced by the reaction of the reducing agent 29 such as unreacted ammonia with the S content. Thus, it is possible to suppress an increase in pressure loss in the flue gas discharging line L12, and the corrosion in the passage of the flue gas discharging line L12, due to deposition of ammonium sulfate, ammonium hydrogen sulfate or the like in the flue gas discharging line L12.

Also, in order to cope with environmental regulations or the like, although the $CO_2$ recovery device 18 is provided to remove $CO_2$ contained in the flue gas 22, in the methods for manufacturing methanol and ammonia which have been conventionally used, as in Patent Literatures 1 and 2, it is necessary to provide the desulfurization device on the upstream side in the gas flow direction of the flue gas from the $CO_2$ recovery device, and the sulfur concentration in the flue gas at the inlet of the $CO_2$ recovery device is required to set to a predetermined value (for example, 1 ppm) or lower. Also, the number of the devices to be installed increases as much as the desulfurization device, a disposition location of each device is limited, and the installation cost increases. In contrast, in the present embodiment, since the S content does not exist in the flue gas 22 discharged from the reformer 14, it is possible to recover $CO_2$ in the flue gas 22, without installing the desulfurization device on the upstream side in the gas flow direction of the flue gas 22 from the $CO_2$ recovery device 18. Therefore, it is possible to reduce the equipment costs required for recovering $CO_2$ in the flue gas 22.

In addition, in the present embodiment, the reforming device 10 is configured so that the first heat exchanger 12 and the second heat exchanger 16 are provided in the flue gas discharging line L12, but is not limited thereto, and the reforming device 10 may be provided with a plurality of heat exchangers for performing the heat-exchange by the flue gas 22.

Figure 2:
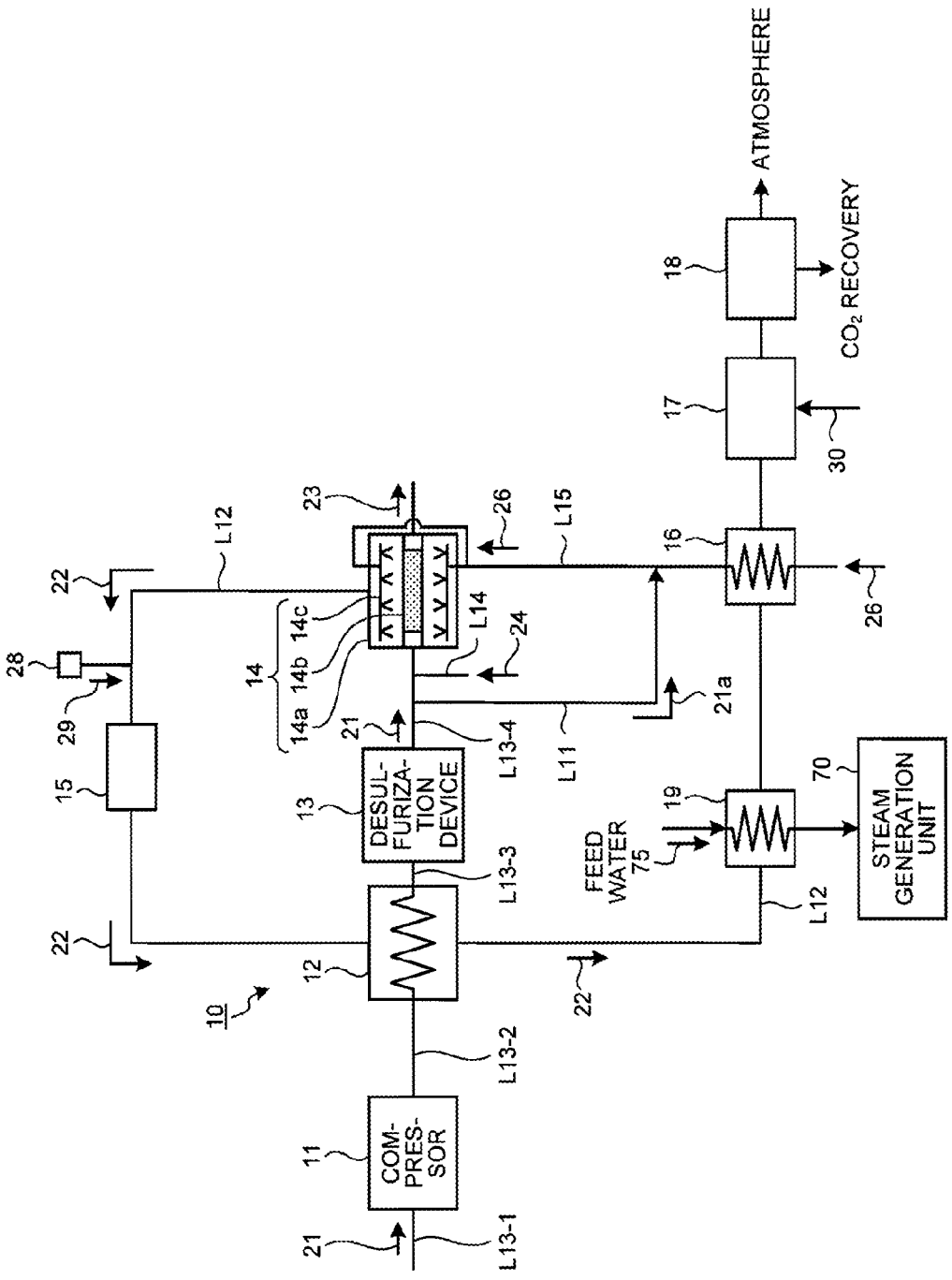
FIG. 2 is a schematic diagram of the reforming device according to the first embodiment of the present invention.

FIG. 2 is a diagram illustrating an example of another configuration of the reforming device 10. As illustrated in FIG. 2, the flue gas discharging line L12 has a third heat exchanger (heat exchange unit) 19 that is interposed between the first heat exchanger 12 and the second heat exchanger 16.

The third heat exchanger 19 is a heat exchanger that saves heat of feed water 75 to be supplied to a steam generation unit 70. By providing the third heat exchanger 19 between the first heat exchanger 12 and the second heat exchanger 16, it is possible to increase the amount of water and the amount of heat of the feed water 75 to be supplied to the steam generation unit 70.

Figure 3:
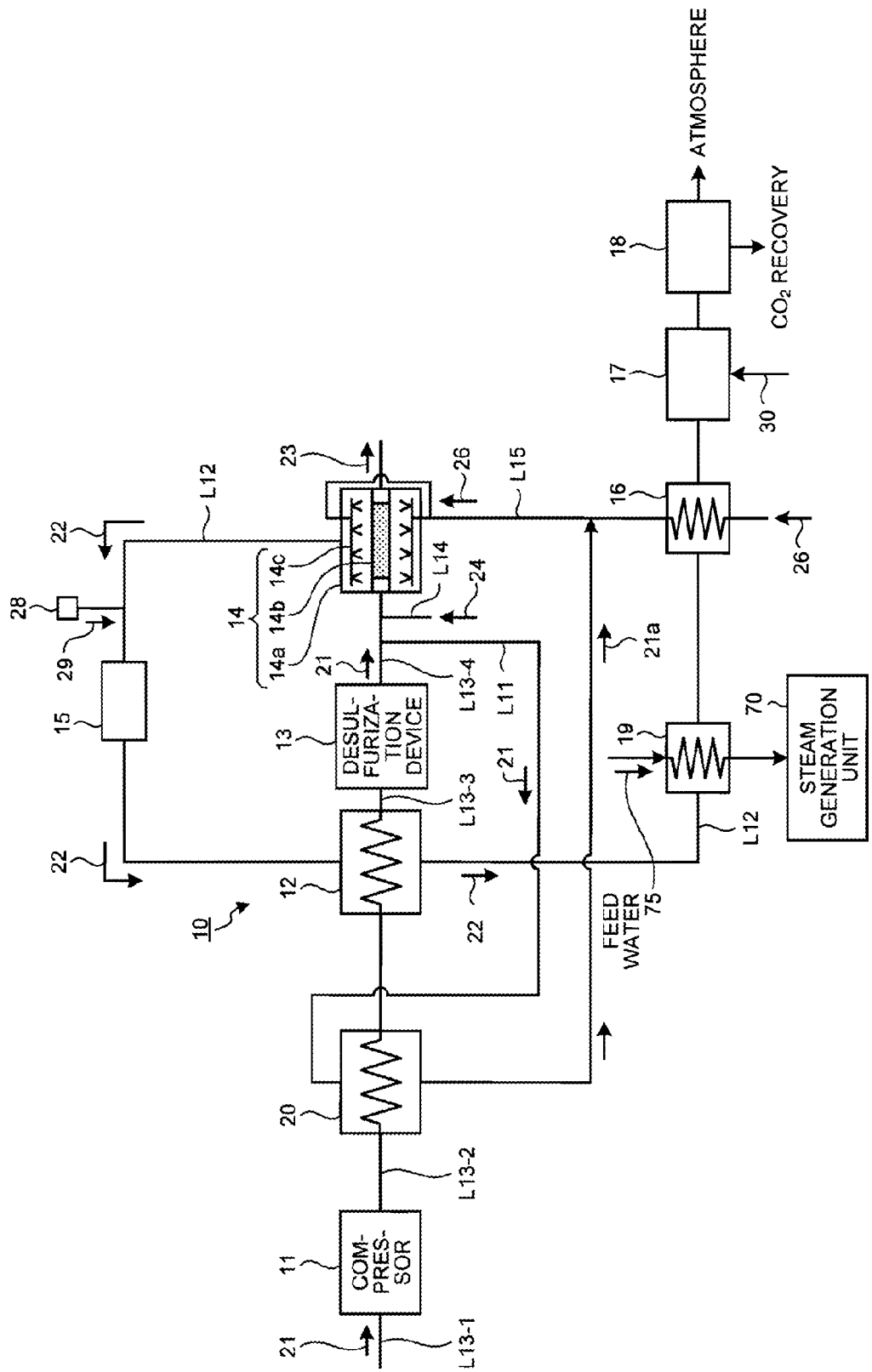
FIG. 3 is a schematic diagram of another reforming device according to the first embodiment of the present invention.

Further, as illustrated in FIG. 3, a fourth heat exchanger (heat exchange unit) 20 is provided between the compressor 11 of the raw material gas supply line L13-2 and the first heat exchanger 12 to save heat of the natural gas 21 to be supplied to the first heat exchanger 12, by the branched natural gas 21*a* after the desulfurization.

By keeping the natural gas 21 to be introduced into the first heat exchanger 12 to the high-temperature side in advance, the fourth heat exchanger 20, which performs the heat-exchange between the natural gases 21, can reduce the amount of recovery heat of the flue gas 22 after the heat exchange to increase the amount of recovery heat in the third heat exchanger 19, as compared to the system illustrated in FIG. 2.

In addition, by raising the temperature of the flue gas 22 to be introduced into the third heat exchanger 19, it is possible to improve the temperature difference of the fluid to be heat-exchanged, thereby reducing the heat transfer area of the third heat exchanger 19.

Figure 4:
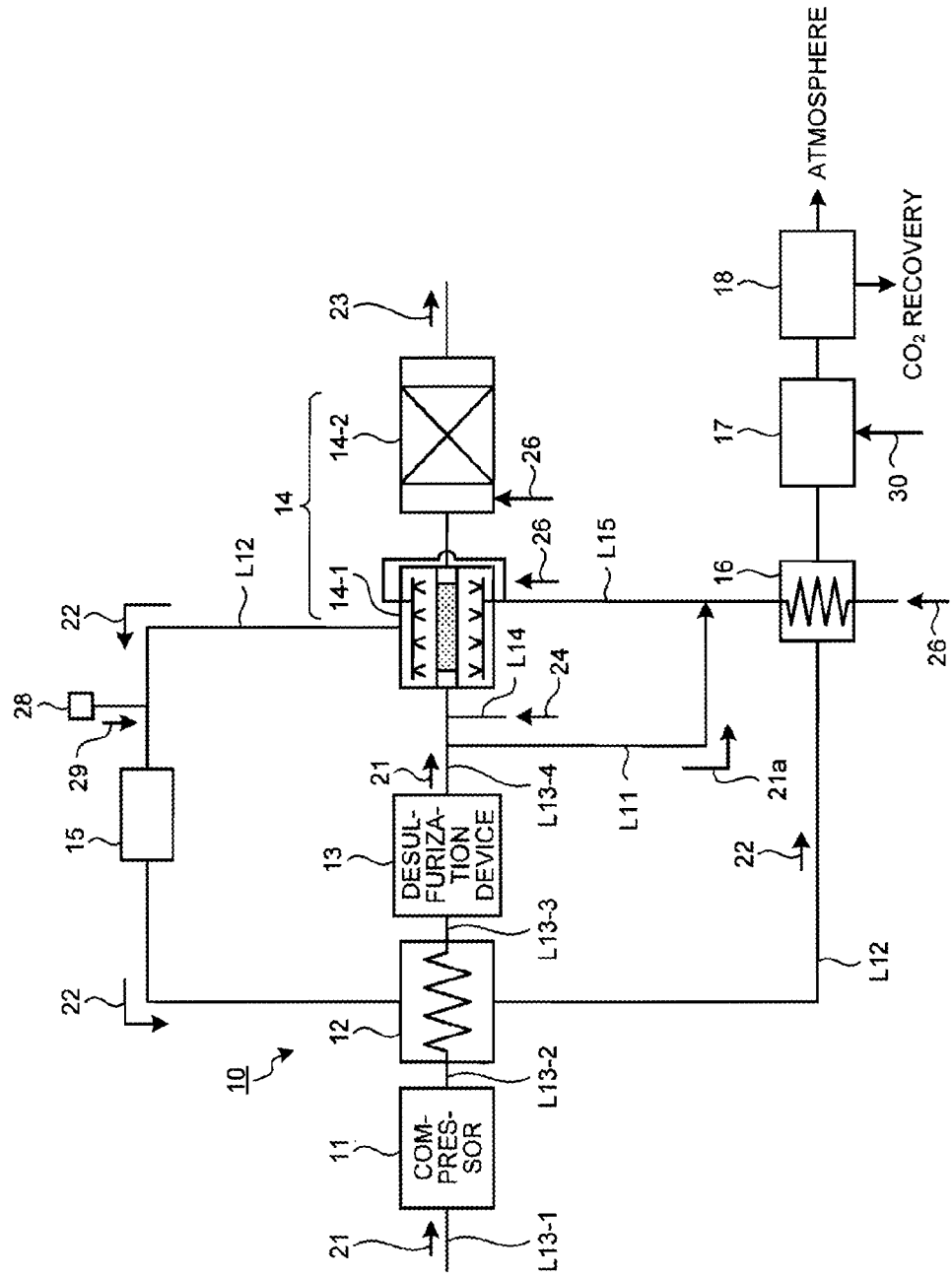
FIG. 4 is a schematic diagram of another reforming device according to the first embodiment of the present invention.

In addition, in the present embodiment, the reforming device 10 is equipped with only one reformer 14, but is not limited thereto, and a plurality of reformers 14 may be equipped. FIG. 4 is a diagram illustrating an example of another configuration of the reforming device 10. As illustrated in FIG. 4, the reformer 14 may have a first reformer 14-1 and a second reformer 14-2.

As illustrated in FIG. 4, the first reformer 14-1 is intended to supply the vapor 24 to the desulfurized and compressed natural gas 21 and primarily reform hydrocarbon in the natural gas 21 to either one or both of $H_2$ and CO or $H_2$ and $CO_2$. The first reformer 14-1 has the same configuration as that of the first reformer 14 illustrated in FIG. 1, and has a main body 14*a* (not illustrated in FIG. 4), a catalyst reaction tube 14*b* (not illustrated in FIG. 4) and a burner 14*c* (not illustrated in FIG. 4). The catalyst reaction tube 14*b* is heated by the flue gas 22 generated by combustion in the burner 14*c*, and the introduced natural gas 21 comes into contact with the reforming catalyst when passing through the reforming catalyst layer of the catalyst reaction tube 14*b*, and thus, as in the above-described formulas (3) and (4), hydrocarbon in the natural gas 21 is subjected to vapor-reforming to either one or both of $H_2$ and CO or $H_2$ and $CO_2$.

After the natural gas 21 is primarily reformed in the first reformer 14-1, it is supplied to the second reformer 14-2.

The second reformer 14-2 is intended to supply air (oxygen) to the reformed gas 23, and secondarily reform hydrocarbon in the reformed gas 23 using a partial oxidation reaction. The heated combustion air 26 is introduced into the second reformer 14-2 from the outside, and hydrocarbon in the reformed gas 23 is secondarily reformed to either one or both of $H_2$ and CO or $H_2$ and $CO_2$.

Figure 5:
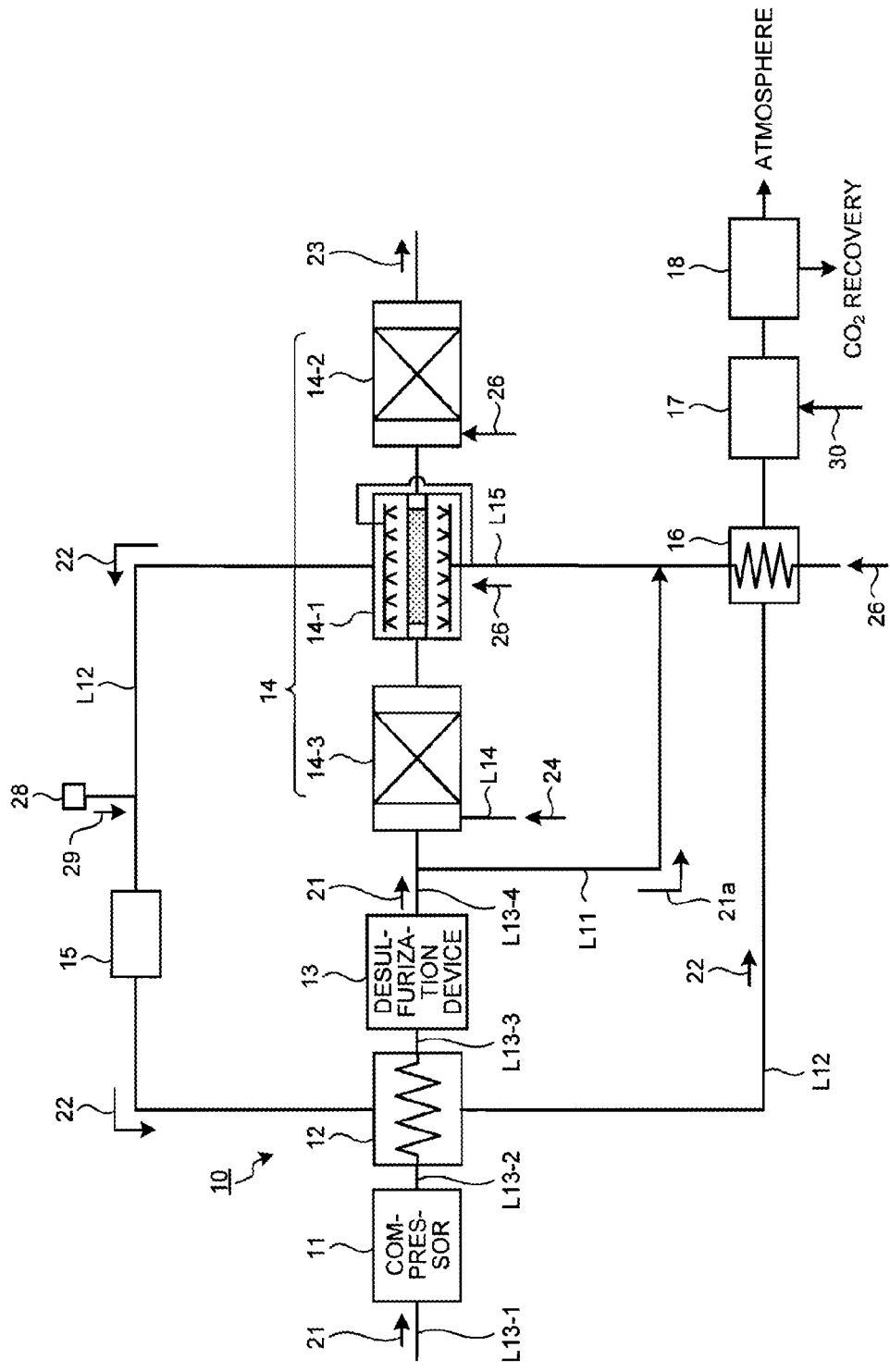
FIG. 5 is a schematic diagram of another reforming device according to the first embodiment of the present invention.

FIG. 5 is a diagram illustrating an example of another configuration of the reforming device 10. As illustrated in FIG. 5, the reformer 14 may have a pre-reformer 14-3, the first reformer 14-1, and the second reformer 14-2.

The pre-reformer 14-3 is intended to supply the vapor 24 to the natural gas 21 and primarily reform hydrocarbon in the natural gas 21 to either one or both of $H_2$ and CO or $H_2$ and $CO_2$. The pre-reformer 14-3 has a main body, and a reforming catalyst layer having a reforming catalyst therein. Also, the pre-reformer 14-3 is connected to the vapor supply line L14. The vapor 24 is supplied into the pre-reformer 14-3 through the vapor supply line L14, and is mixed with the natural gas 21. After the natural gas 21 is mixed with the vapor 24 in the main body, the natural gas 21 is supplied to the reforming catalyst layer. The natural gas 21 comes into contact with the reforming catalyst when passing through the reforming catalyst layer in the pre-reformer 14-3, and thus, as in the above-described formulas (3) and (4), hydrocarbon in the natural gas 21 is primarily reformed to either one or both of $H_2$ and CO or $H_2$ and $CO_2$.

When the reformer 14 is constituted by three stages of the first reformer 14-1, the second reformer 14-2 and the pre-reformer 14-3, a part or all of the flue gas 22 discharged from the first reformer 14-1 may be used as a heating medium for heating the reforming catalyst layer of the pre-reformer 14-3.

Figure 6:
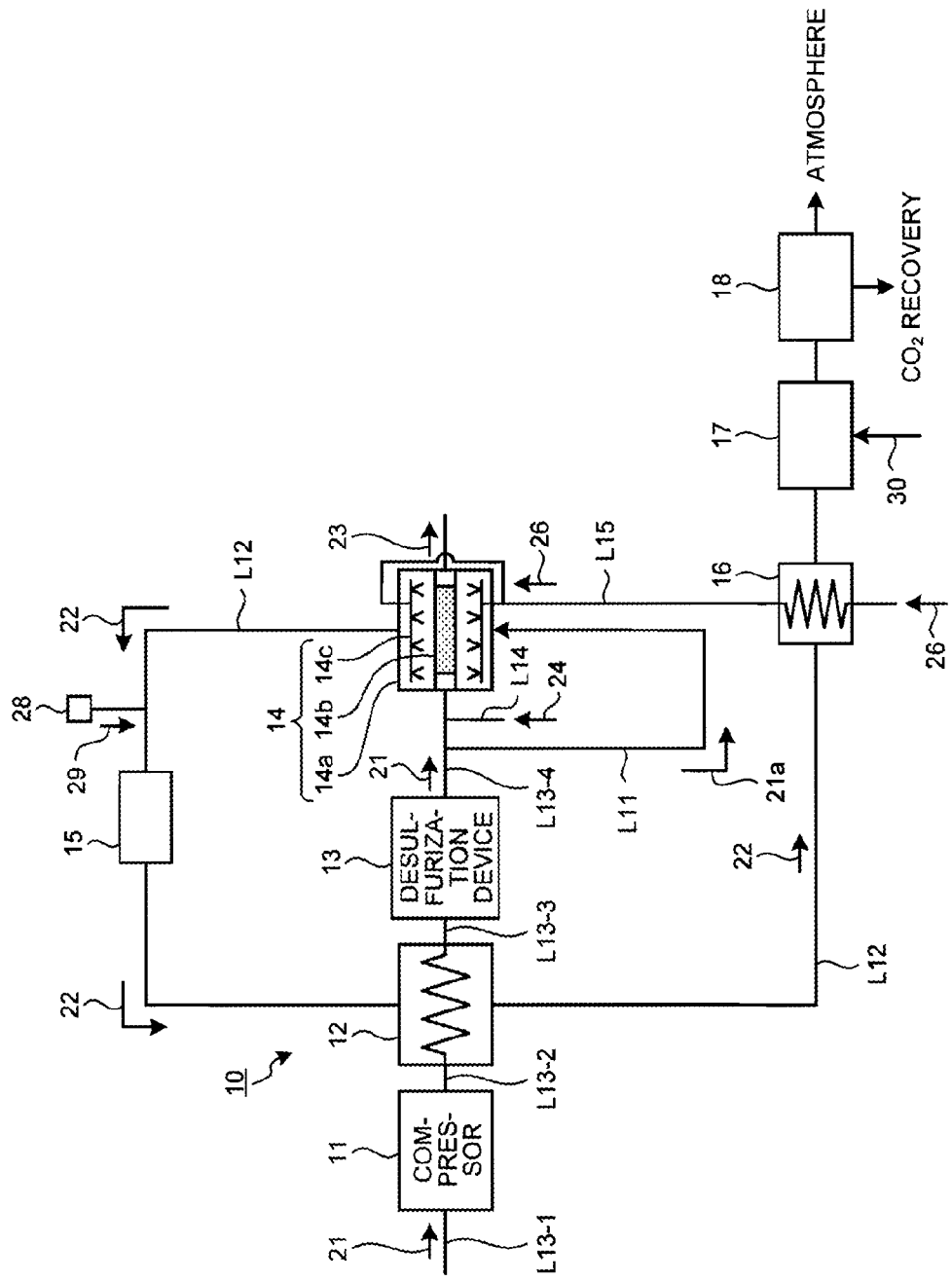
FIG. 6 is a schematic diagram of another reforming device according to the first embodiment of the present invention.
Figure 7:
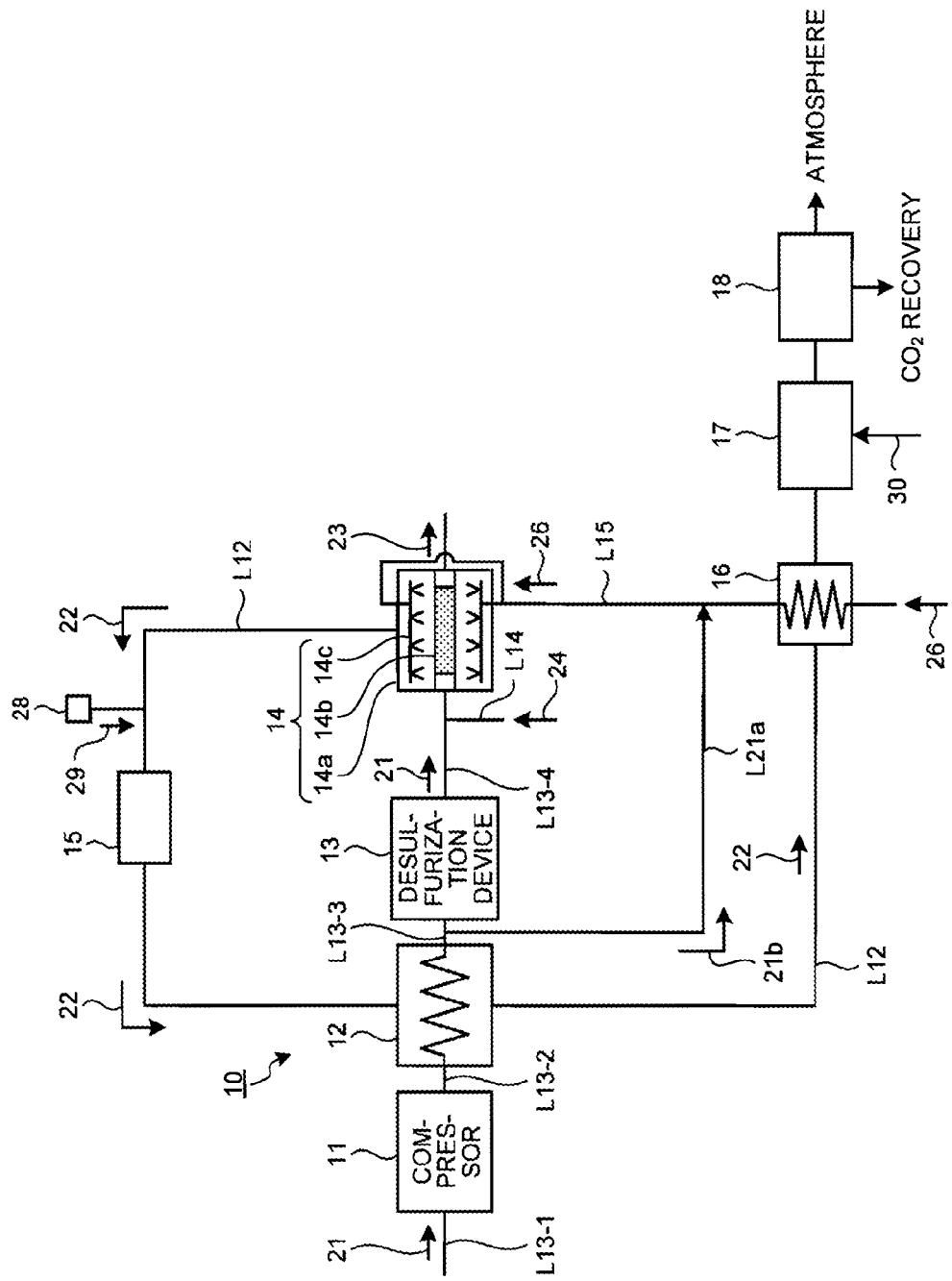
FIG. 7 is a schematic diagram of another reforming device according to the first embodiment of the present invention.
Figure 8:
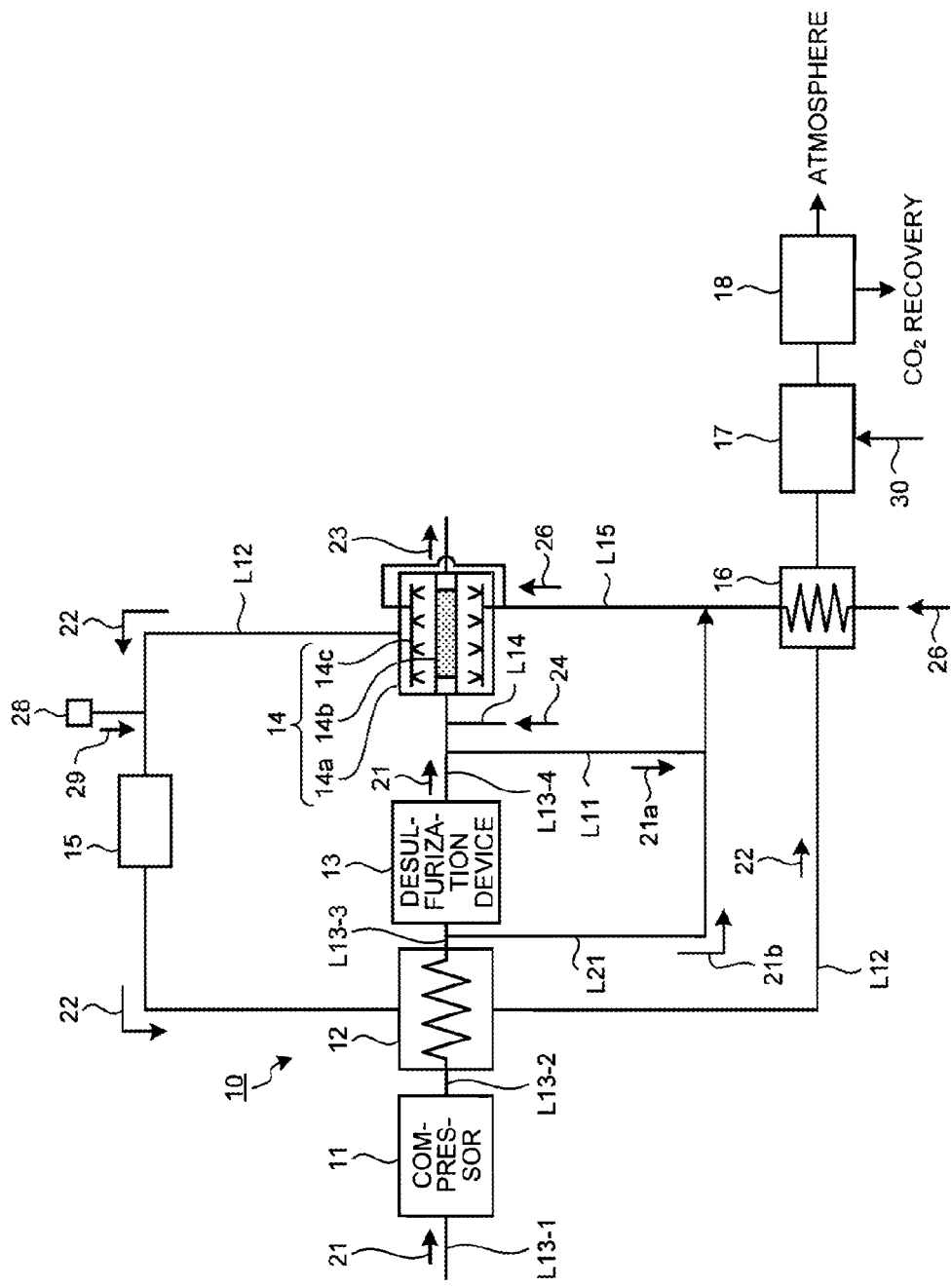
FIG. 8 is a schematic diagram of another reforming device according to the first embodiment of the present invention.

FIGS. 6 to 8 are diagrams illustrating modified examples of another configuration of the reforming device 10.

In this embodiment, the raw material gas branching line L11 is provided so as to be connected to the air supply line L15 so that the natural gas 21 and the combustion air 26 are supplied to the reformer 14 through the air supply line L15, but is not limited thereto, and as illustrated in FIG. 6, the raw material gas branching line L11 may be directly connected to the reformer 14 so that the natural gas 21 and the combustion air 26 are separately supplied into the reformer 14.

In addition, in the present embodiment, although the raw material gas branching line L11 is provided so as to be connected to the downstream side of the desulfurization device 13 with respect to the flow direction of the natural gas 21, but is not limited thereto, and as illustrated in FIG. 7, a raw material gas branching line L21*a* for connecting the upstream side of the desulfurization device 13 with the air supply line L15 may be provided such that the raw material gas branching line L21*a* extracts the branch gas 21*b* of a part of the natural gas 21 from the upstream side of the desulfurization device 13 with respect to the flow direction of the natural gas 21.

In addition, as illustrated in FIG. 8, the raw material gas branching lines L11 and L21 may be provided so as to extract 21*a* of a part of the natural gas 21 from the upstream side and the downstream side of the desulfurization device 13 with respect to the flow direction of the natural gas 21.

Furthermore, in the present embodiment, the reforming device 10 is equipped with the denitrification device 15, but is not limited thereto, and the reforming device 10 may not be equipped with the denitrification device 15.

Furthermore, in the present embodiment, the reforming device 10 is equipped with the cooling device 17 and the $CO_2$ recovery device 18, but is not limited thereto, and the reforming device 10 may not be equipped with these devices in a case where there is no need for recovery of $CO_2$ contained in the flue gas 22.

As described above, since the reforming device 10 has the characteristics as described above, it can be used for manufacturing the chemical products, using the reformed gas 23 obtained in the reforming device 10. Specifically, the chemical products include, for example, ammonia, methanol, urea, hydrogen, and liquid fuel of liquid hydrocarbon such as wax, diesel oil, kerosene, and gasoline by FT synthesis. In particular, by applying the reforming device 10 to the manufacturing system of ammonia and methanol and the manufacturing system of urea and methanol, it is possible to improve the manufacturing efficiency of methanol and ammonia, and the manufacturing efficiency of urea and methanol.

Figure 9:
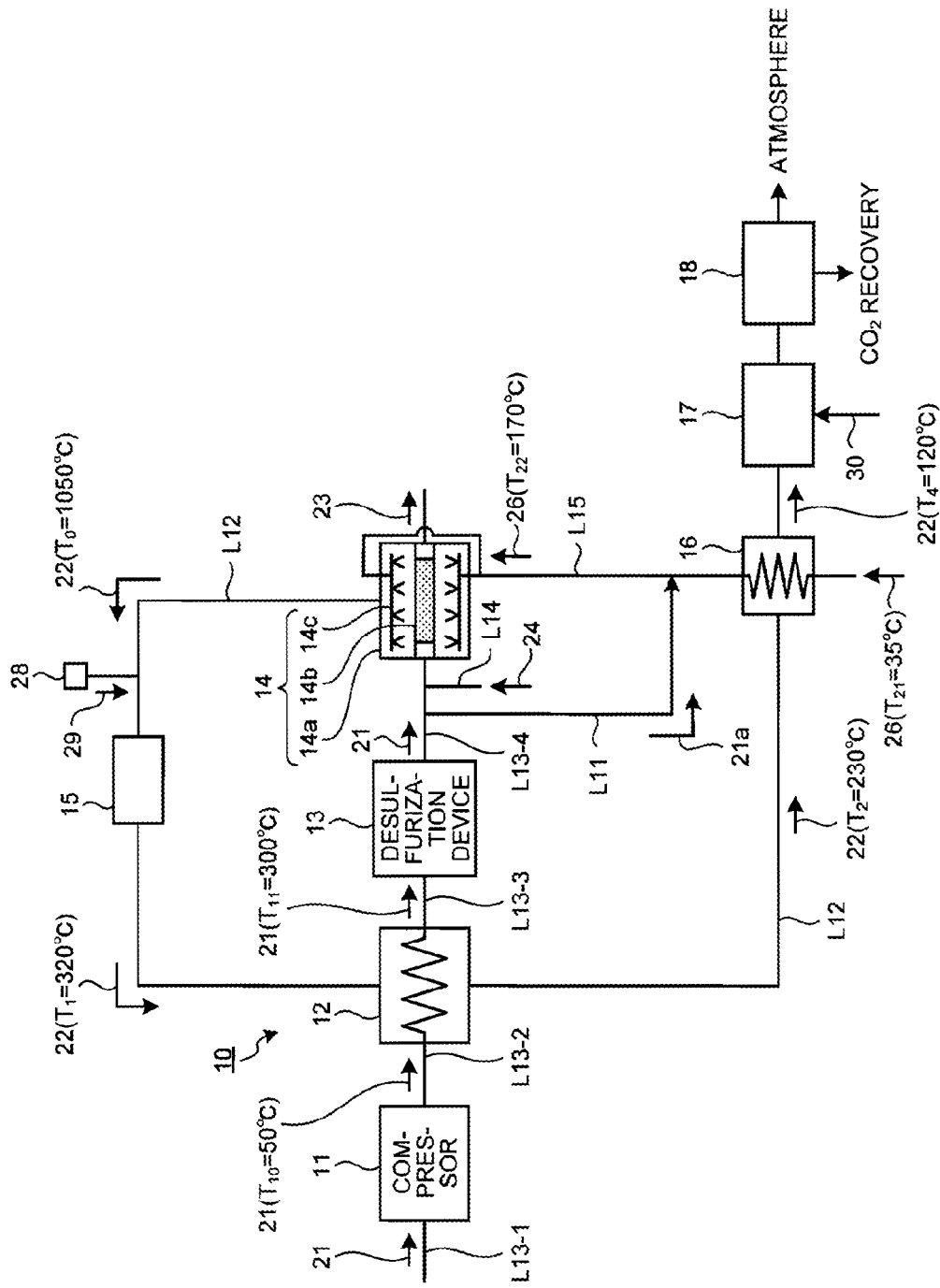
FIG. 9 is a diagram illustrating an example of a system configuration of the reforming device illustrated in FIG. 1.
Figure 10:
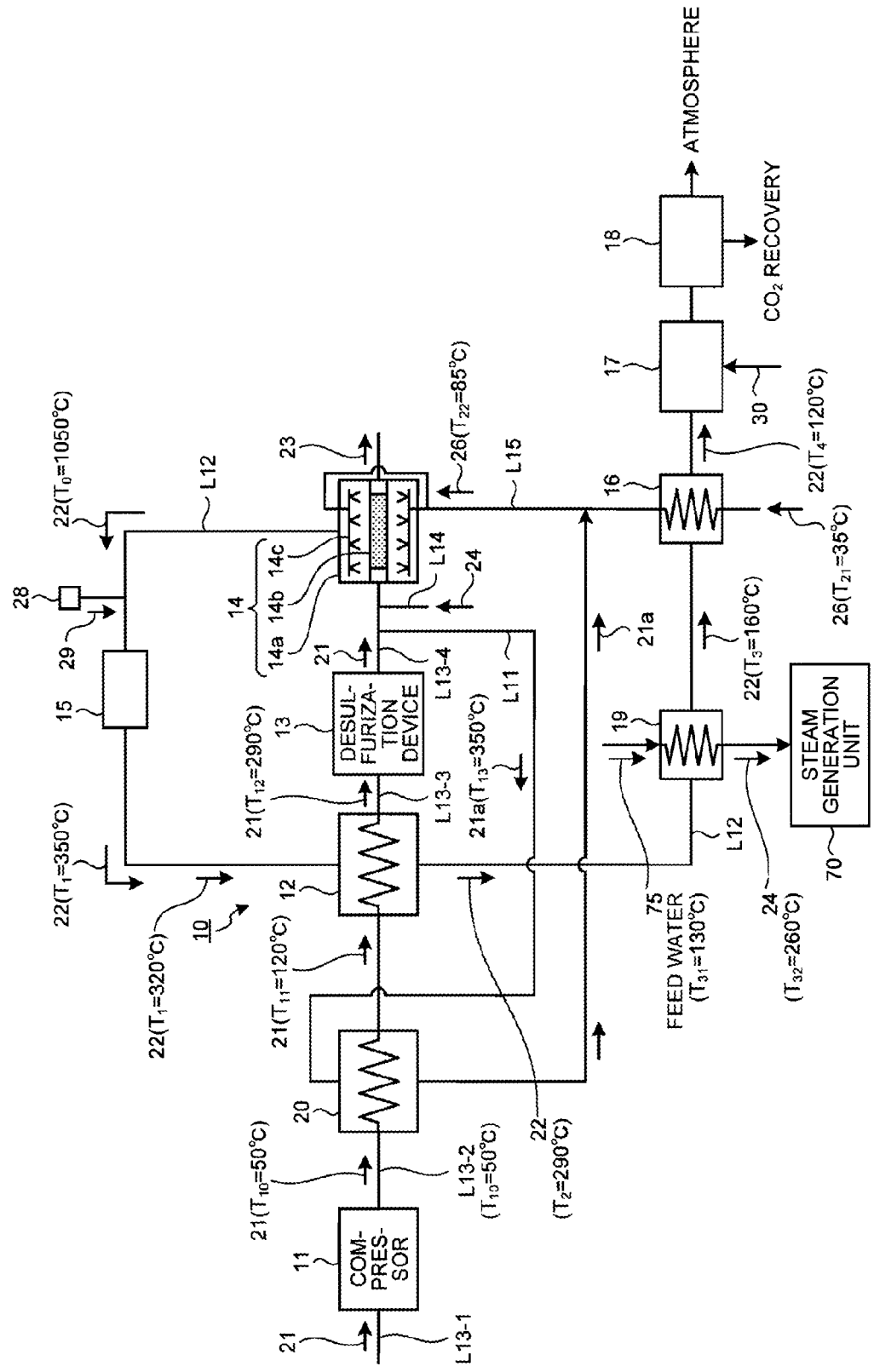
FIG. 10 is a diagram illustrating an example of a system configuration of the reforming device illustrated in FIG. 3.

FIGS. 9 and 10 are diagrams illustrating examples of system configurations of the reforming device illustrated in FIG. 1 and the reforming device illustrated in FIG. 3.

FIG. 9 is an example of a system configuration corresponding to the reforming device illustrated in FIG. 1, and the flue gas 22 introduced into the flue gas discharging line L12 from the reformer 14 is heat-exchanged in a plurality of heat exchange units provided inside the flue gas duct.

First, as illustrated in FIG. 9, in the first heat exchanger 12 that initially heat-exchanges the natural gas 21 compressed by the compressor 11 and having the temperature ($T_{10}=50°$ C.), the natural gas 21 is heat-exchanged with the flue gas 22 having the temperature ($T_1=320°$ C.). The natural gas 21 introduced into the first heat exchanger 12 is heat-exchanged to a high temperature from the temperature ($T_{10}=50°$ C.) to the temperature ($T_{12}=300°$ C.). Thereafter, the heated natural gas 21 passes through the desulfurization device 13, is further heat-exchanged in a heat exchanger (not illustrated), and is introduced into the reformer 14 side. Although the flue gas 22 from the reformer 14 is discharged at a high temperature of the temperature ($T_0=1050°$ C.), the flue gas 22 is heat-recovered by a heat exchanger (not illustrated), and becomes to have the temperature of about 320° C. on a downstream side of the denitrification device 15.

The flue gas 22 after the heat-exchange in the first heat exchanger 12 is lowered to a temperature ($T_2=230°$ C.), and on the downstream side of the flue gas discharging line L12, the flue gas 22 is heat-exchanged with the combustion air 26 in the second heat exchanger 16. Through the heat-exchange in the second heat exchanger 16, the flue gas 22 is lowered to a temperature ($T_4=120°$ C.) from a temperature ($T_2=230°$ C.) to heat the combustion air 26. By the heat-exchange in the second heat exchanger 16, the combustion air 26 can have a high temperature from a temperature ($T_{21}=35°$ C.) to a temperature ($T_{21}=170°$ C.) Since the temperature of the reformer 14 becomes a high temperature side, it is possible to reduce an amount of branch of the natural gas 21 to be introduced into the reformer 14 in the flue gas discharging line L12, thereby improving the amount of introduction of the natural gas 21 for reforming.

FIG. 10 is an example of the system configuration corresponding to the reforming device illustrated in FIG. 3.

In this example, the natural gas 21 compressed by the compressor 11 and having a temperature ($T_{10}=50°$ C.) is initially heat-exchanged by a natural gas 21a (temperature $T_{13}=350°$ C.) of a part of the natural gas 21 in a fourth heat exchanger 20. As a result of the heat-exchange in the fourth heat exchanger 20, the natural gas 21 can be heated from the temperature ($T_{10}=50°$ C.) to the temperature ($T_{11}=120°$ C.). The heated natural gas 21 is then heat-exchanged with the flue gas 22 having the temperature ($T_1=350°$ C.) in the first heat exchanger 12 and is heated to a temperature ($T_{12}=290°$ C.). The heated natural gas 21 is then heated to about 360° C. by a heat exchanger which is not illustrated, passes through the desulfurization device 13, is further heat-exchanged in a heat exchanger which is not illustrated, and is introduced into the reformer 14 side. Although the flue gas 22 from the reformer 14 is discharged at a high temperature of the temperature ($T_0=1050°$ C.), the flue gas 22 is heat-recovered by a heat exchanger (not illustrated), and becomes to have the temperature of about 350° C. on the downstream side of the denitrification device 15.

The flue gas 22 after the heat-exchange in the first heat exchanger 12 is lowered to a temperature ($T_2=290°$ C.), and on its downstream side, the flue gas 22 is heat-exchanged with the feed water 75 to be introduced into the steam generation unit 70 in the third heat exchanger 19. By the heat-exchange with the feed water 75 in the third heat exchanger 19, the flue gas 22 is lowered from a temperature ($T_2=290°$ C.) to a temperature ($T_3=160°$ C.), thereby heating the feed water 75 from a temperature ($T_{31}=130°$ C.) to a temperature ($T_{32}=260°$ C.). The heated feed water 75 is introduced into the steam generation unit 70.

Thereafter, the flue gas 22 having the temperature ($T_3=160°$ C.) after the heat-exchange in the third heat exchanger 19 is heat-exchanged with the combustion air 26 in the second heat exchanger 16. Through the heat-exchange in the second heat exchanger 16, the flue gas 22 is lowered from a temperature ($T_2=160°$ C.) to a temperature ($T_4=120°$ C.), thereby heating the combustion air 26. Through the heat-exchange in the second heat exchanger 16, the combustion air 26 is heated from a temperature ($T_{21}=35°$ C.) to a temperature ($T_{21}=85°$ C.)

In this example, by heating the feed water 75 to be introduced into the steam generation unit 70 in the third heat exchanger 19, it is possible to obtain the boiler feed water having a temperature ($T_{32}=260°$ C.), and it is possible to increase the overall amount of steam generation.

As a result, since the amount of water of the feed water 75 of the vapor generation to be introduced into the steam generation unit 70 increases by the reforming system of FIG. 10, the amount of steam generation is improved by about 20t/h compared to the case of the reforming system of FIG. 9, and it is possible to achieve a reduction of 1.9% in the product basic unit of ammonia (Gcal/ton-$NH_3$) including the installation of an auxiliary boiler.

Second Embodiment

<Manufacturing Device of Chemical Products>

Next, an example of the case of applying the reforming device 10 according to the first embodiment illustrated in FIG. 1 to the manufacturing device of chemical products will be described with reference to the drawings. The manufacturing device of chemical products has the reforming device 10, and a chemical product generation unit that manufactures the chemical products using the reformed gas 23 obtained by the reforming device 10. In this embodiment, the case of manufacturing ammonia, methanol or urea as the chemical products will be described.

[Manufacturing Example of Ammonia]

Figure 11:
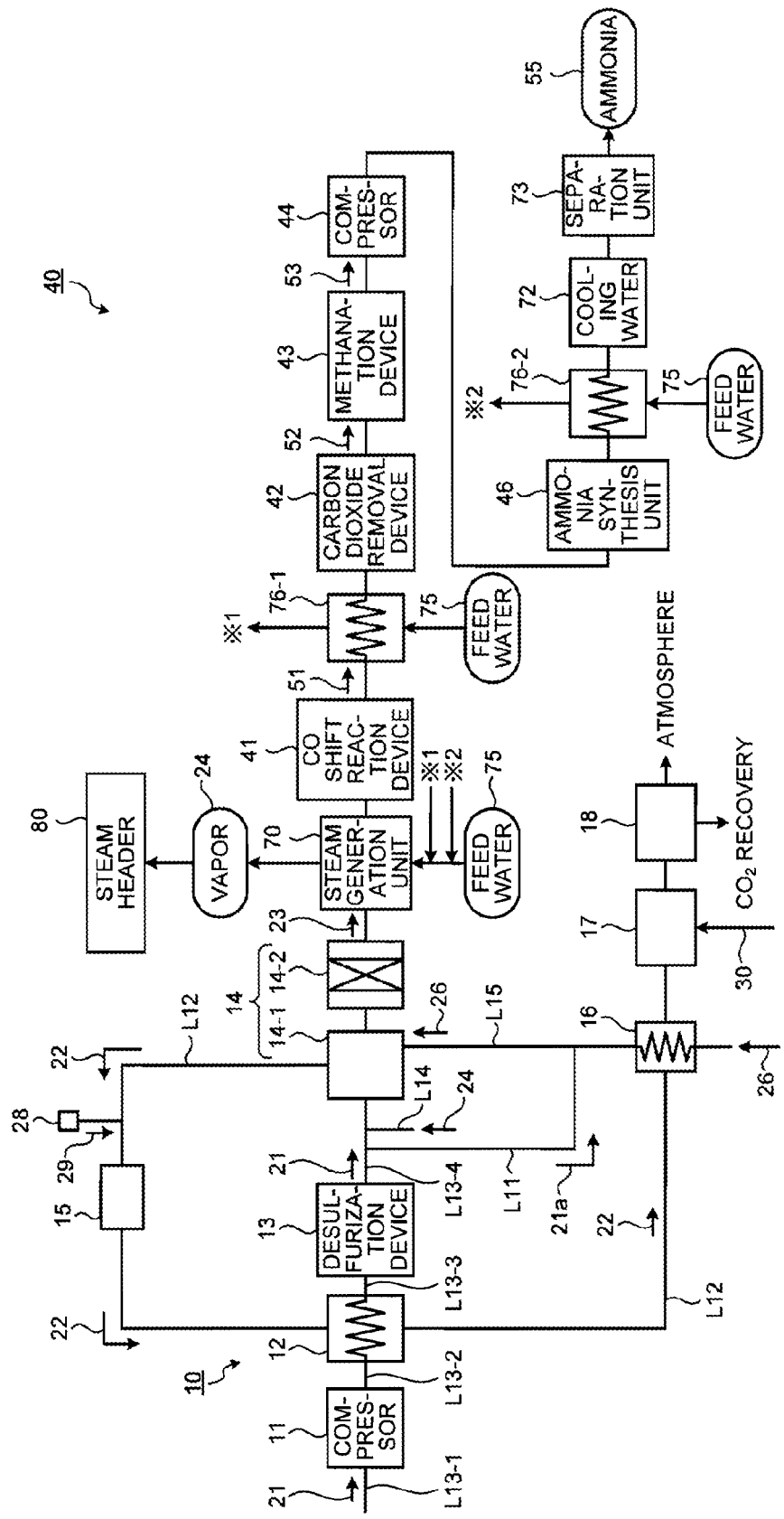
FIG. 11 is a schematic diagram of a chemical product manufacturing device equipped with a reforming device according to a second embodiment of the present invention.

FIG. 11 is a schematic diagram of a chemical product manufacturing device equipped with the reforming device according to a second embodiment of the present invention. In the present embodiment, the reforming device having the two-stage configuration illustrated in FIG. 4 is used. Since the same configurations as those of the reforming device according to the first embodiment illustrated in FIG. 4 are identical, the repeated description will not be provided. In this example, the reformer is configured so that the primary reformer 14 has a primary reformer 14-1 and a secondary reformer 14-2, but the present invention is not limited thereto.

As illustrated in FIG. 11, a chemical product manufacturing device 40 for manufacturing ammonia has a reforming device 10, a steam generation unit 70, a CO shift reaction device (CO shift reaction unit) 41, a carbon dioxide removal device (carbon dioxide removal unit) 42, a methanation device (methanation unit) 43, a compressor 44, a hydrogen separation device (hydrogen separation unit) 45, an ammonia synthesis unit 46, a cooling unit 72, and a separation unit 73. In addition, in the present embodiment, the CO shift reaction device 41, the carbon dioxide removal device 42, the methanation device 43, compressors 44-1 and 44-2, the hydrogen separation device 45 and the ammonia synthesis unit 46 form a chemical product generation unit.

In addition, two first and second preliminary heating units 76-1 and 76-2, which preliminarily heat the feed water 75 to be supplied to the steam generation unit 70, are interposed between the CO shift reaction device (CO shift reaction unit) 41 and the carbon dioxide removal device (carbon dioxide removal unit) 42, and between the ammonia synthesis unit 46 and the cooling unit 72. In addition, in FIG. 11, a steam header 80 supplies the vapor obtained by the steam generation unit 70. Furthermore, the vapor from an auxiliary boiler or the like is also introduced into the steam header, and a required amount of vapor is sent to each vapor supply destination from here.

(Steam Generation Unit)

The steam generation unit 70 is intended to supply the vapor 24 to the steam header 80 in the system. The steam generation unit 70 is provided with a waste heat recovery boiler (WHB) which recovers the waste heat of the reformed gas 23, and a superheater. After the steam generation unit 70 thermally heats the feed water 75 by the waste heat to obtain the heated vapor, the steam generation unit 70 further overheats the heated vapor by the superheater and sends the vapor 24 to the steam header 80. In addition, in this system, the waste heat recovery boiler may be further installed on the downstream side of the passage line of the reformed gas 23 and on the downstream side of the ammonia synthesis unit 46 to recover the heat, but the waste heat recovery boiler is not provided in this embodiment.

(CO Shift Reaction Device)

The CO shift reaction device 41 is intended to convert (shift) CO in the reformed gas 23 to $CO_2$ and generate a shift gas 51 containing $CO_2$. As the CO shift reaction device 41, for example, a CO shift reactor equipped with a filling unit filled with the CO shift reaction catalyst which converts (shift) CO to $CO_2$ is used.

The reformed gas 23 obtained by reforming the natural gas 21 in the reforming device 10 is discharged from the reforming device 10 and is supplied to the CO shift reaction device 41. In the CO shift reaction device 41, as in the following formula (6), CO in the reformed gas 23 is converted to $CO_2$ to generate a shift gas 51 containing $CO_2$. In addition, the gas temperature of the shift gas 51 is, for example, in the range of 150° C. to 1000° C.

$$CO + H_2O \rightarrow CO_2 + H_2 \tag{6}$$

The shift gas 51 generated by the CO shift reaction device 41 is discharged from the CO shift reaction device 41 and is supplied to the carbon dioxide removal device 42.

(Carbon Dioxide Removal Device)

The carbon dioxide removal device 42 is intended to remove carbon dioxide ($CO_2$) in the shift gas 51. As the carbon dioxide removal device 42, for example, a device which removes $CO_2$ in the shift gas 51 by utilizing a chemical adsorption using $CO_2$ absorbent such as an amine solvent, a device having catalyst for removing $CO_2$, a membrane separation device having a separation membrane which separates $CO_2$ in the shift gas 51 or the like is used. The carbon dioxide removal device 42 removes $CO_2$ in the shift gas 51 to generate a $CO_2$ removal gas 52 from which $CO_2$ is removed. Also, the gas temperature of the $CO_2$ removal gas 52 is, for example, about 50° C.

The carbon dioxide removal device 42 separates $CO_2$ from the shift gas 51. In addition, separated $CO_2$ may be used as a gas for methanol synthesis.

The $CO_2$ removal gas 52 discharged from the carbon dioxide removal device 42 is supplied to the methanation device 43.

(Methanation Device)

The methanation device 43 is intended to convert $CO_2$ in the $CO_2$ removal gas 52, from which $CO_2$ is removed by the carbon dioxide removal device 42, into methane. As the methanation device 43, for example, a methanation reactor (methanator) having a catalyst portion filled with methanation catalyst inside or the like is used. The reaction temperature (methanation temperature) at the catalyst portion is preferably 220° C. or higher and 450° C. or lower, and more preferably, 290° C. or higher and 350° C. or lower, from the viewpoint of the limit temperature at which the methanation catalyst can be used.

In the methanation device 43, as in the following formula (7), $CO_2$ in the $CO_2$ removal gas 52 is converted into methane to generate a $CO_2$ removal gas 53 containing methane.

$$CO_2 + 4H_2 \rightarrow CH_4 + 2H_2O \tag{7}$$

The $CO_2$ removal gas 53 discharged from the methanation device 43 is supplied to the compressor 44.

(Compressor)

The compressor 44 is intended to compress the $CO_2$ removal gas 53.

After raising the pressure of the $CO_2$ removal gas 53 by the compressor 44, the $CO_2$ removal gas 53 is supplied to the hydrogen separation device 45.

(Ammonia Synthesis Unit)

The ammonia synthesis unit 46 is intended to manufacture ammonia ($NH_3$) 55 after converting $CO_2$ in the $CO_2$ removal gas 53 into methane by the methanation device 43. It is possible to use an ammonia synthesis unit 46 that has been generally used hitherto, and, for example, it is possible to adopt an ammonia synthesis reactor in which the catalyst is disposed on one or more beds in the reactor. A method for synthesizing ammonia by causing the $CO_2$ removal gas 53 as a synthesis gas containing nitrogen ($N_2$) and hydrogen to flow through the ammonia synthesis reactor is used.

In the ammonia synthesis unit 46, as in the following formula (8), nitrogen and hydrogen in the $CO_2$ removal gas 53 react with each other to generate ammonia 55.

$$N_2 + 3H_2 \rightarrow 2NH_3 \tag{8}$$

After the ammonia composite obtained in the ammonia synthesis unit 46 passes through the second preheating unit 76-2, the ammonia composite is cooled by the cooling unit 72, and the objective ammonia 55 is separated by the separation unit 73.

In this way, according to the chemical product manufacturing device 40 for manufacturing ammonia, it is possible to improve the thermal efficiency when reforming the natural gas 21 by providing the above-described reforming device 10, and it is possible to suppress an occurrence of corrosion in the passage of the flue gas discharging line L12 in the course of processing the flue gas 22. Therefore, according to the chemical product manufacturing device 40 that manufactures ammonia, it is possible to stably produce the ammonia 55 and to improve the production efficiency of the ammonia 55.

Moreover, since the sulfur content is removed in the desulfurization device 13, it is possible to lower the temperature of the flue gas 22 after the heat exchange to 120° C., and it is possible to increase the heat exchange efficiency in the second heat exchanger 16 of the flue gas discharging line L12. That is, since the sulfur content is not removed in the related art, the temperature of the flue gas 22 can only be lowered to about 175° C., the amount of introduction of the branch fuel increases accordingly, and as a result, the amount of production of the reformed gas decreases.

Therefore, according to the chemical product manufacturing device of the present embodiment, since it is possible to raise the temperature of the combustion air 26 to be introduced into the reformer 14, it is possible to reduce an amount of branch of the natural gas 21 that is introduced to the reformer 14 by being branched. As a result, since it is possible to achieve an increase in the amount of production of the reformed gas, it is possible to increase the amount of manufacturing of ammonia.

In this way, in this embodiment, since the amount of branch of the branch gas in the raw material gas branching line L11 of the natural gas 21 is reduced, the amount of introduction of the natural gas 21 to be introduced into the reformer 14 is improved by 8.5%. As a result, it is also possible to achieve reduction of 1.1% in the product basic unit (Gcal/ton-NH$_3$) as for an overall efficiency of the plant.

Figure 12:
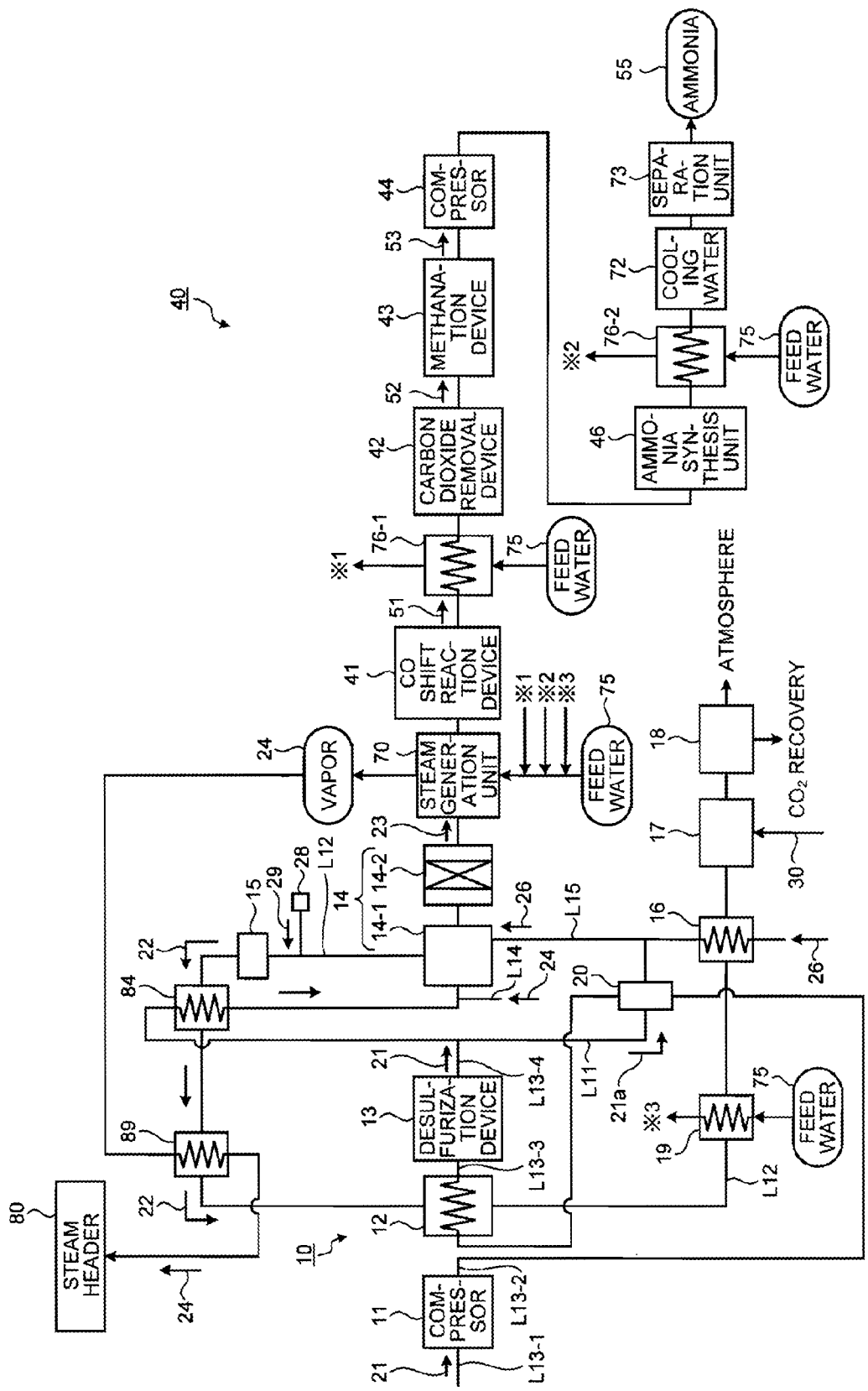
FIG. 12 is a schematic diagram of a chemical product manufacturing device equipped with another reforming device according to the second embodiment of the present invention.

Next, the chemical product manufacturing device using the reforming device illustrated in FIG. 3 of the above-described embodiment will be described. FIG. 12 is a schematic diagram of the chemical product manufacturing device equipped with the reforming device illustrated in FIG. 3 according to the second embodiment of the present invention. In addition, the reforming device illustrated in FIG. 3 is configured so that the reformer 14 is one stage, but in this example, a reformer of a two-stage configuration is adopted as illustrated in FIG. 4.

In the reforming device 10 of the chemical product manufacturing device 40 illustrated in FIG. 12, a third heat exchanger 19 is interposed between the first heat exchanger 12 and the second heat exchanger 16 provided in the flue gas discharging line L12. Thus, since it is possible to heat the feed water 75 supplied to the steam generation unit 70 by the third heat exchanger 19, the amount of generation of vapor greatly increases. In addition, in the reforming device 10 illustrated in FIG. 12, a steam superheater 89, which heat-exchanges the vapor 24 from the steam generation unit 70, is provided in the flue gas discharging line L12. Thus, since the vapor 24 supplied to the steam header 80 is overheated by the flue gas 22 of a high temperature (for example, 890° C.), the temperature of the vapor can be set to a higher temperature (for example, 515° C.)

Thus, in the chemical product manufacturing device as illustrated in FIG. 11, for example, when the amount of vapor generation is insufficient, by providing a separate auxiliary boiler, the vapor is supplied by the auxiliary boiler. However, in the chemical product manufacturing device illustrated in FIG. 12, since the amount of vapor generation greatly increases, the auxiliary boiler may not be required or the auxiliary boiler can be significantly reduced in size.

Thus, according to the chemical product manufacturing device 40 for manufacturing ammonia, it is possible to improve the thermal efficiency when reforming the natural gas 21 by providing the reforming device 10, and it is possible to suppress an occurrence of corrosion in the passage of the flue gas discharging line L12 in the course of processing the flue gas 22. Therefore, according to the chemical product manufacturing device 40 of the present embodiment, it is possible to stably produce the ammonia 55 and to improve the production efficiency of the ammonia 55.

[Manufacturing Example of Urea]

Figure 13:
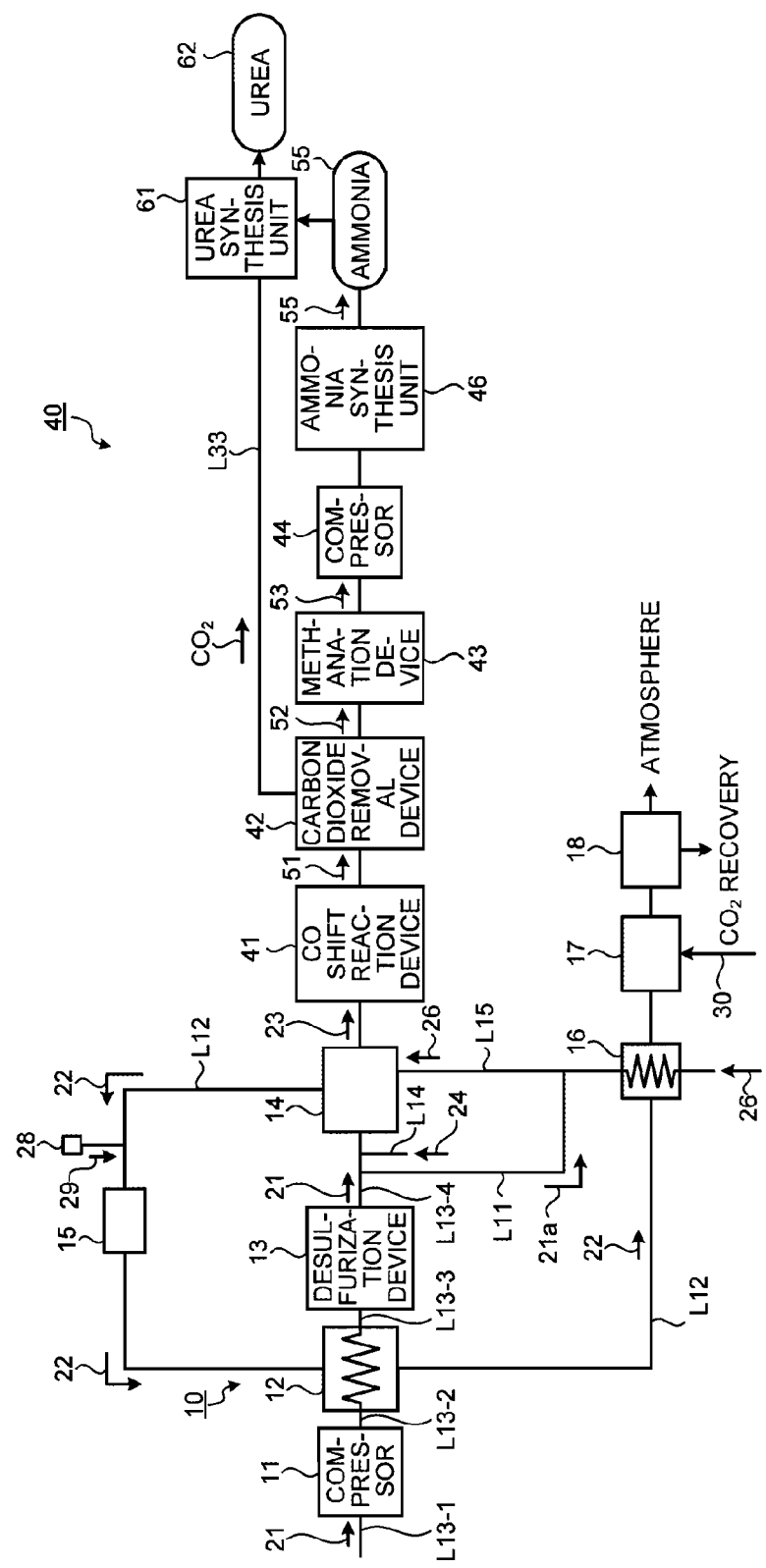
FIG. 13 is a schematic diagram of a chemical product manufacturing device equipped with another reforming device according to the second embodiment of the present invention.

FIG. 13 is a schematic diagram of the chemical product manufacturing device equipped with the reforming device according to the second embodiment of the present invention.

FIG. 13 is a schematic diagram of a manufacturing system of urea and methanol according to the second embodiment of the present invention. As illustrated in FIG. 13, a chemical product manufacturing device 40 for manufacturing urea is further equipped with a urea synthesis unit 61 and a carbon dioxide branching supply line L33, in the chemical product manufacturing device 40 illustrated in FIG. 12.

The urea synthesis unit 61 is provided on the downstream side in the ammonia flow direction of the ammonia synthesis unit 46. The urea synthesis unit 61 is intended to synthesize a urea 62 using the ammonia 55 obtained in the ammonia synthesis unit 46. It is possible to use the urea synthesis unit 61 which has been generally used hitherto, and for example, it is possible to adopt a urea synthesis tube in which ammonia and CO$_2$ react with each other in the tube.

The carbon dioxide branching supply line L33 is a line that introduces CO$_2$, which has been removed by the carbon dioxide removal device 42, into the urea synthesis unit 61.

The ammonia 55 obtained in the ammonia synthesis unit 46 is supplied to the urea synthesis unit 61. In addition, CO$_2$ is supplied from the carbon dioxide removal device 42 to the urea synthesis unit 61 via the carbon dioxide supply line L33.

In the urea synthesis unit 61, the ammonia 55 obtained in the ammonia synthesis unit 46 and CO$_2$ separated by the carbon dioxide removal device 42 react with each other as in the following reaction formula (9) to synthesize urea (NH$_2$(CO)NH$_2$).

$$2NH_3 + CO_2 \rightarrow NH_2(CO)NH_2 + H_2 \tag{9}$$

Thus, in the chemical product manufacturing device 40 that manufactures urea, it is possible to manufacture the urea 62, using the ammonia 55 obtained in the ammonia synthesis unit 46 and CO$_2$ separated by the carbon dioxide removal device 42 during the ammonia synthesis.

In this way, similar to the chemical product manufacturing device 40 that manufactures ammonia according to the second embodiment, according to the chemical product manufacturing device 40 that manufactures urea, by providing the reforming device 10 of the first embodiment, it is possible to improve the thermal efficiency when reforming the natural gas 21, and it is possible to suppress an occurrence of corrosion in the passage of the flue gas discharging line L12 in the course of processing the flue gas 22. Therefore, according to the chemical product manufacturing device 40 that manufactures urea, it is possible to stably produce the urea 62 and to improve the production efficiency of the urea 62.

[Simultaneous Manufacturing Example of Ammonia and Methanol]

Figure 14:
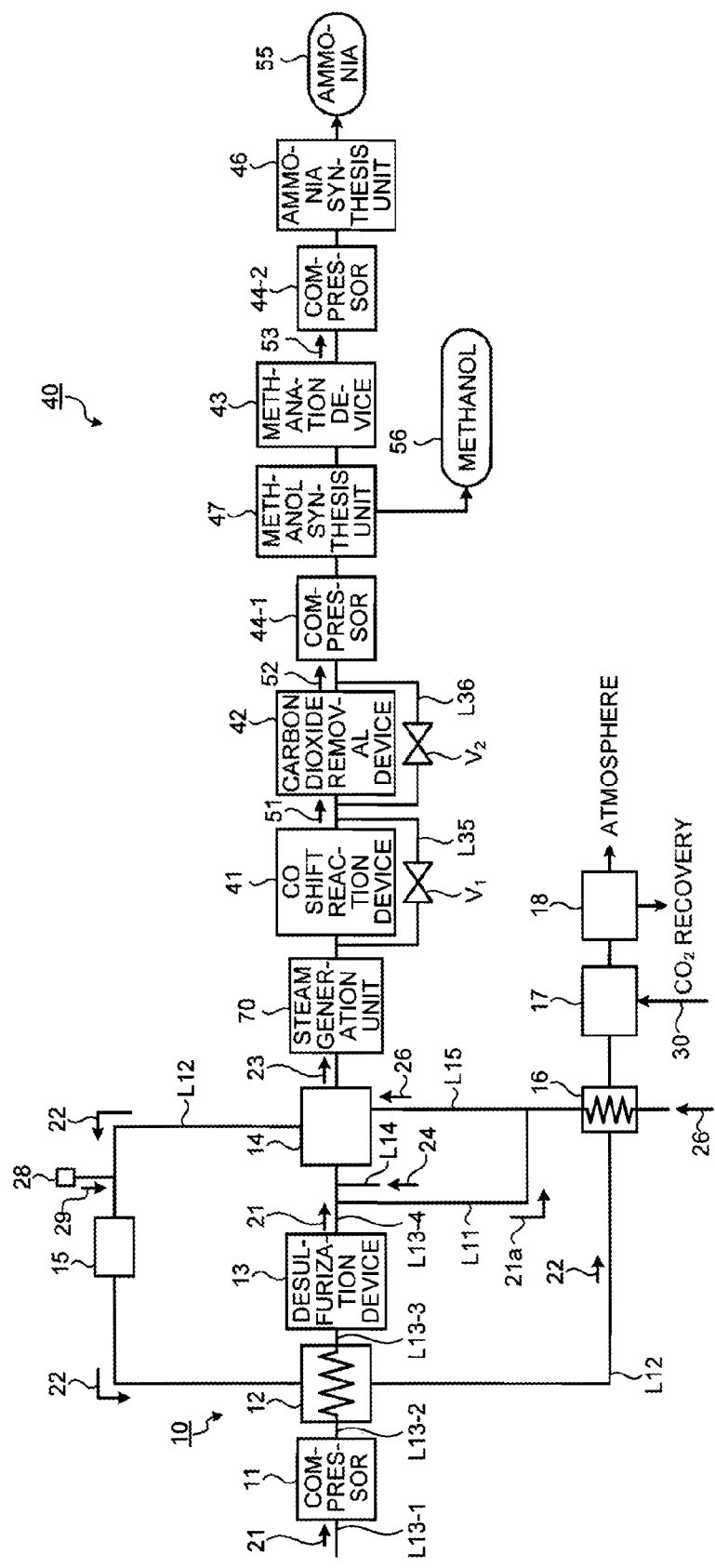
FIG. 14 is a schematic diagram of a chemical product manufacturing device equipped with another reforming device according to the second embodiment of the present invention.

FIG. 14 is a schematic diagram of the chemical product manufacturing device equipped with the reforming device according to a second embodiment of the present invention. In the above-described embodiments, ammonia or urea has been manufactured alone. However, in the present embodiment, as the chemical product manufacturing device, a device capable of simultaneously manufacturing methanol as well as ammonia is provided.

As illustrated in FIG. 14, the chemical product manufacturing device 40 for manufacturing of ammonia and methanol has a reforming device 10, a CO shift reaction device (CO shift reaction unit) 41, a carbon dioxide removal device (carbon dioxide removal unit) 42, a methanation device (methanation unit) 43, first and second compressors 44-1 and 44-2, an ammonia synthesis unit (ammonia synthesis unit) 46, and a methanol synthesis unit 47.

In the chemical product manufacturing device 40 of the present embodiment, the methanol synthesis unit 47 is installed on the upstream side of the methanation device 43. Moreover, as the compressor 44, the first compressor 44-1 is installed between the carbon dioxide removal device 42 and the methanol synthesis unit 47, and the second compressor 44-2 is installed between the methanation device 43 and the ammonia synthesis unit 46. Furthermore, in this embodiment, although the compressor 44 has a two-stage configuration, it may have a plurality of stages such as a three-stage configuration of a low-pressure compressor, an intermediate-pressure compressor and a high-pressure compressor.

(Methanol Synthesis Unit)

The methanol synthesis unit 47 is intended to synthesize the methanol 56 that uses carbon dioxide and hydrogen in the reformed gas 23 obtained in the reforming device 10 as a raw material. It is possible to use the methanol synthesis unit 47 that has been generally used hitherto, and for example, a methanol synthesis device having a catalytic reactor or the like is used.

Here, carbon dioxide in the reformed gas 23 as a methanol production raw material adjusts its content, by providing bypass lines L35 and L36 each having on-off valves $V_1$ and $V_2$ that partially bypass the CO shift reaction device 41 and the carbon dioxide removal device 42.

In the methanol synthesis unit 47, as in the following formulas (10) and (11), hydrogen and carbon monoxide in the reformed gas 23 react with each other and hydrogen and carbon dioxide react with each other to produce the methanol 56.

$$2H_2 + CO \rightarrow CH_3OH \quad (10)$$

$$3H_2 + CO_2 \rightarrow CH_3OH + H_2O \quad (11)$$

Thus, according to the chemical product manufacturing device 40 that manufactures ammonia and methanol, it is possible to obtain the ammonia 55 obtained in the ammonia synthesis unit 46 and the methanol 56 obtained in the methanol synthesis unit 47, and it is possible to simultaneously manufacture the ammonia 55 and the methanol 56 in parallel.

Thus, according to the chemical product manufacturing device 40 that manufactures ammonia and methanol, by providing the reforming device 10 of the first embodiment, similar to the chemical product manufacturing device 40 that manufactures ammonia according to the second embodiment, it is possible to improve the thermal efficiency when reforming the natural gas 21 and it is possible to prevent the occurrence of corrosion in the passage of the flue gas discharging line L12 in the course of processing the flue gas 22. Therefore, according to the chemical product manufacturing device 40 that manufactures urea, it is possible to stably produce the ammonia 55 and the methanol 56 and to improve their production efficiency.

[Simultaneous Manufacturing Example of Urea and Methanol]

Figure 15:
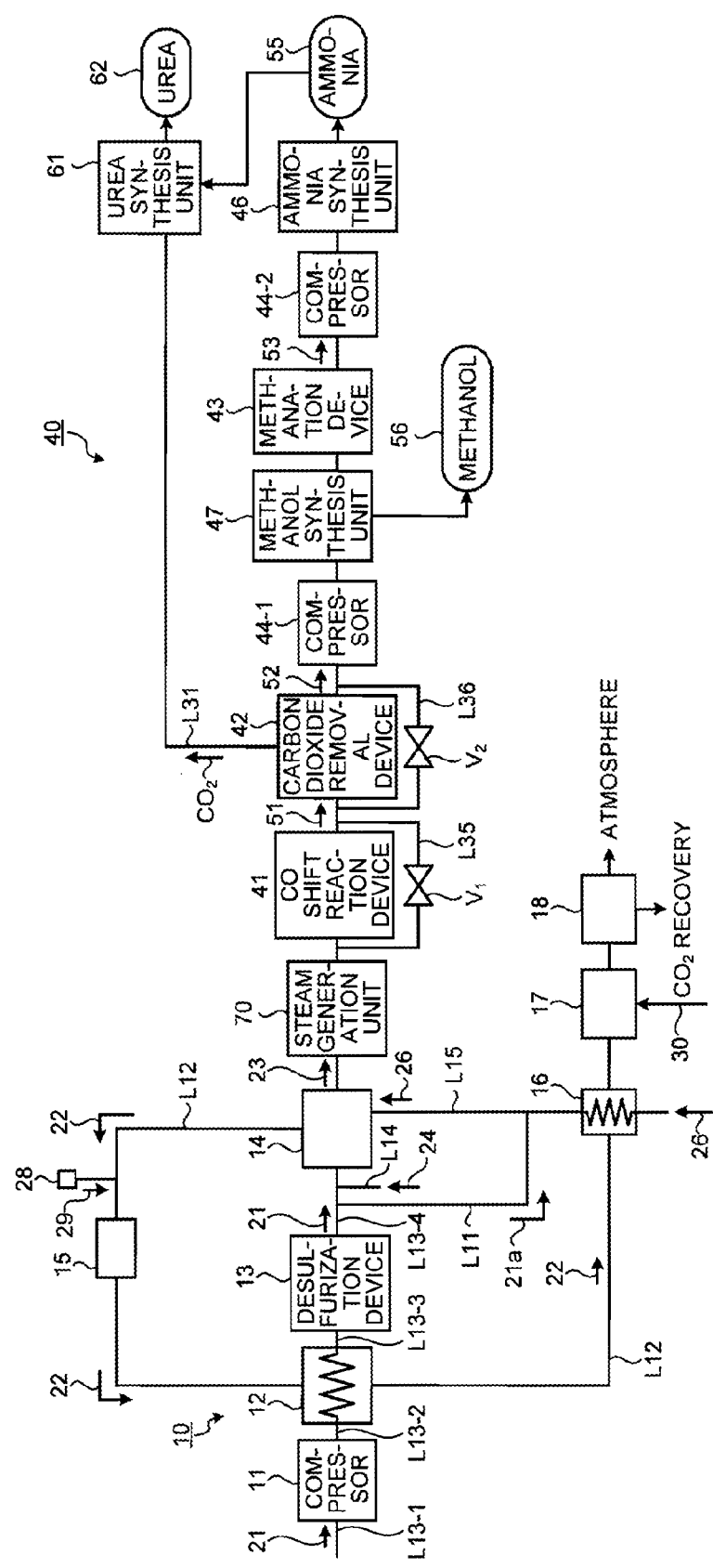
FIG. 15 is a schematic diagram of a chemical product manufacturing device equipped with another reforming device according to the second embodiment of the present invention.

FIG. 15 is a schematic diagram of a chemical product manufacturing device equipped with the reforming device according to the second embodiment of the present invention. Although ammonia and methanol have been manufactured in the above-described embodiments, in this embodiment, as a chemical product manufacturing device, there is provided a device capable of manufacturing urea and simultaneously manufacturing methanol, by using ammonia as a raw material.

In the chemical product manufacturing device 40 of FIG. 14, the ammonia 55 obtained in the ammonia synthesis unit 46 is further introduced into the urea synthesis unit 61 to manufacture urea.

Thus, according to the chemical product manufacturing device 40 that manufactures urea and methanol, it is possible to obtain the urea 62 using the ammonia 55 obtained in the ammonia synthesis unit 46 as a raw material, and the methanol 56 obtained in the methanol synthesis unit 47, and it is possible to simultaneously obtain the urea 62 and the methanol 56 in parallel.

In this way, according to the chemical product manufacturing device 40 that manufactures urea and methanol, by providing the reforming device 10 of the first embodiment, similar to the chemical product manufacturing device 40 that manufactures ammonia according to the second embodiment, it is possible to improve the thermal efficiency when reforming the natural gas 21 and it is possible to suppress the occurrence of corrosion in the passage of the flue gas discharging line L12 in the course of processing the flue gas 22. Therefore, according to the chemical product manufacturing device 40 that manufactures urea, it is possible to stably produce the urea 62 and the methanol 56 and to improve their production efficiency.

[Simultaneous Manufacturing Example of Ammonia and Methanol]

Figure 16:
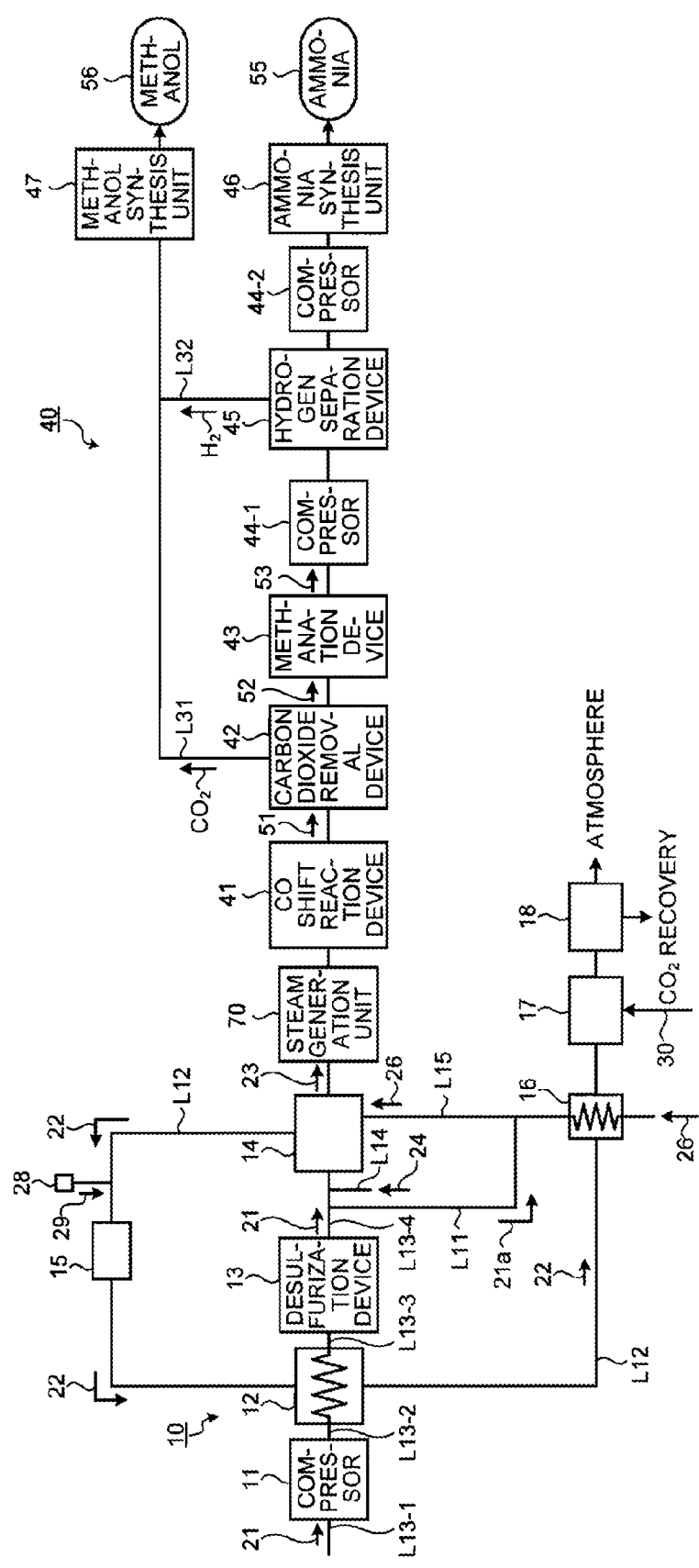
FIG. 16 is a schematic diagram of a chemical product manufacturing device equipped with another reforming device according to the second embodiment of the present invention.

FIG. 16 is a schematic diagram of a chemical product manufacturing device equipped with the reforming device according to the second embodiment of the present invention. In the embodiment of FIG. 14, although methanol has been manufactured by the reformed gas 23, in the present embodiment, as the chemical product manufacturing device, a device capable of manufacturing methanol by the additional methanol synthesis unit by separating carbon dioxide and hydrogen from the reformed gas 23 is provided.

As illustrated in FIG. 16, a hydrogen separation device 45 is provided between the first compressor 44-1 and the second compressor 44-2.

(Hydrogen Separation Device)

The hydrogen separation device 45 provided between the first compressor 44-1 and the second compressor 44-2 is intended to separate a part of hydrogen ($H_2$) contained in the $CO_2$ removal gas 53 from the $CO_2$ removal gas 53. The hydrogen separation device 45 is a membrane separation device having a hydrogen-permeable function membrane. In this embodiment, the hydrogen-permeable function membrane is a membrane for separating at least a part of hydrogen ($H_2$) contained in the gas.

As the hydrogen-permeable function membrane, for example, it is preferred to use a palladium (Pd) membrane, a polymer membrane such as polysulfone, polyamide or polyimide, or a membrane obtained by a plurality of bundles of elements formed into a hollow fiber. As the hydrogen-permeable function membrane, it is possible to adopt the most suitable design, based on the material, the use condition, the life, the hydrogen permeation coefficient, and the selection rate.

In the hydrogen separation device 45, since the $CO_2$ removal gas 53 transmits through the hydrogen-permeable function membrane, hydrogen contained in the $CO_2$ removal gas 53 is separated by the hydrogen permeable function membrane. The $CO_2$ removal gas 53 in which hydrogen is separated by the hydrogen separation device 45 is discharged from the hydrogen separation device 45.

The hydrogen separation device 45 is connected to the hydrogen supply line L32, a part of hydrogen ($H_2$) separated from the shift gas 51 in the hydrogen separation device 45 is supplied to the methanol synthesis unit 47 through the hydrogen supply line L32, and is used as a gas for methanol synthesis.

In addition, in this embodiment, as the hydrogen separation device 45, a membrane separation device equipped with the hydrogen-permeable function membrane is used, but is not limited thereto, and, for example, it is possible to use a pressure swing adsorption device (PSA) or the like, and any device capable of separating at least a part of hydrogen contained in the $CO_2$ removal gas 53 may be used.

The $CO_2$ removal gas 53 discharged from the hydrogen separation device 45 is supplied to the second compressor 44-2. After the pressure of the $CO_2$ removal gas 53 is appropriately adjusted to a pressure suitable for ammonia synthesis in the second compressor 44-2, the $CO_2$ removal gas 53 is supplied to the ammonia synthesis unit 46. Furthermore, hydrogen separated by the hydrogen separation device 45 is supplied to the methanol synthesis unit 47 through a hydrogen supply line L32.

Hydrogen separated by the hydrogen separation device 45 passes through the hydrogen supply line L32, $CO_2$ separated by the carbon dioxide removal device 42 passages through the carbon dioxide supply line L31, and hydrogen separated by the hydrogen separation device 45 and carbon dioxide ($CO_2$) separated by the carbon dioxide removal device 42 are supplied to the methanol synthesis unit 47.

(Methanol Synthesis Unit)

The methanol synthesis unit 47 is intended to synthesize the methanol 56, by using carbon dioxide separated by the carbon dioxide removal device 42 and hydrogen separated by the hydrogen separation device 45, as the raw materials. It is possible to use the methanol synthesis unit 47 that has been generally used hitherto, and for example, a methanol synthesis device having a catalytic reactor or the like is used.

Thus, according to the chemical product manufacturing device 40 that manufactures the ammonia 55 and the methanol 56, it is possible to obtain the ammonia 55 obtained in the ammonia synthesis unit 46, and the methanol 56, by using carbon dioxide separated by the carbon dioxide removal device 42 and hydrogen separated by the hydrogen separation device 45, and it is possible to simultaneously manufacture the ammonia 55 and the methanol 56 in parallel.

In this way, according to the manufacturing system 40 that manufactures ammonia and methanol, by providing the reforming device 10, it is possible to improve the thermal efficiency when reforming the natural gas 21, and it is possible to suppress the occurrence of corrosion in the passage of the flue gas discharging line L12 in the course of processing the flue gas 22. Therefore, according to the manufacturing system 40 of ammonia and methanol, it is possible to stably produce the ammonia 55 and the methanol 56 and to improve the production efficiency of the ammonia 55 and the methanol 56.

In addition, in the present embodiment, the hydrogen separation device 45 is provided between the first compressor 44-1 and the second compressor 44-2 to separate hydrogen in all $CO_2$ removal gas 53 separated by the hydrogen separation device 45. However, the above-described configuration is not limited, and only a part of the $CO_2$ removal gas 53 separated by the first compressor 44-1 or the second compressor 44-2 may be supplied to the hydrogen separation device 45 to separate hydrogen in the $CO_2$ removal gas 53 by the hydrogen separation device 45.

[Simultaneous Manufacturing of Urea and Methanol]

Figure 17:
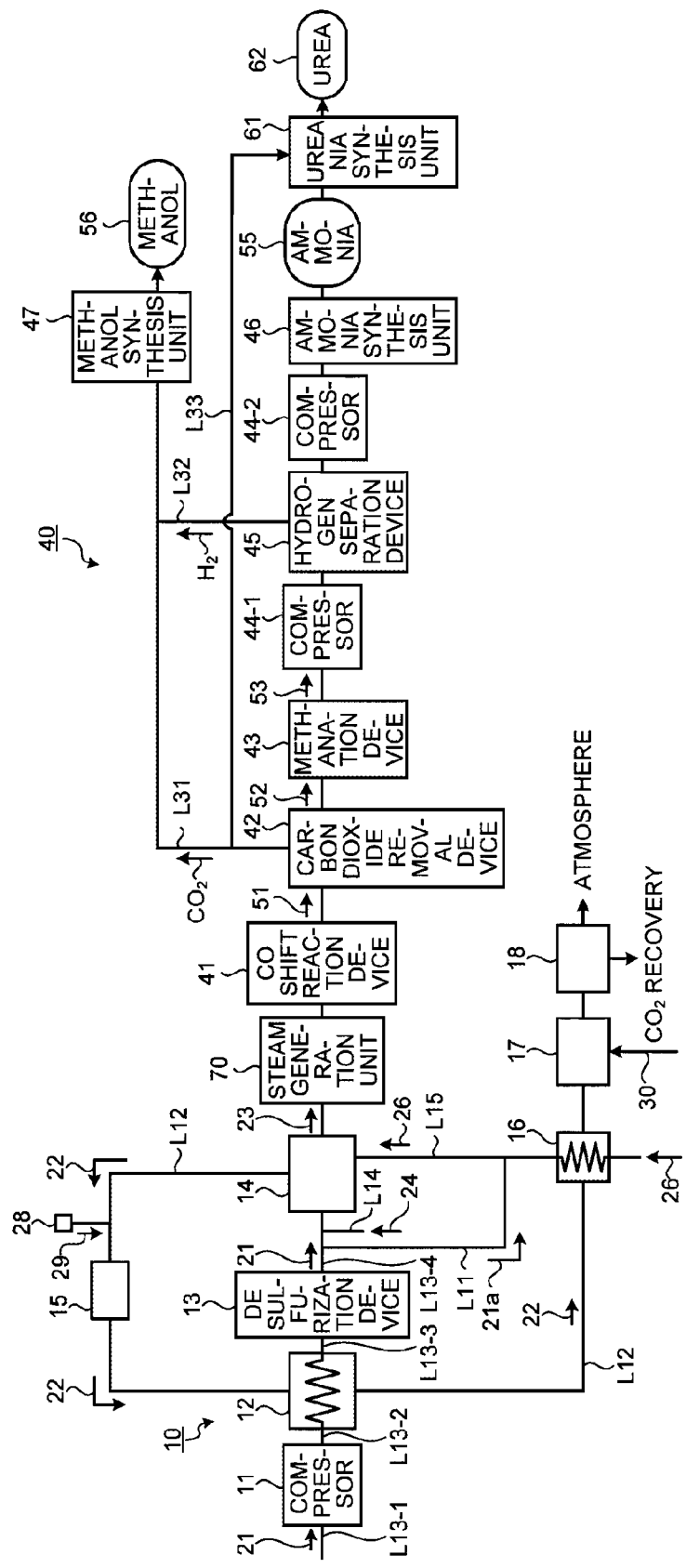
FIG. 17 is a schematic diagram of a chemical product manufacturing device equipped with another reforming device according to the second embodiment of the present invention.

FIG. 17 is a schematic diagram of a chemical product manufacturing device equipped with the reforming device according to the second embodiment of the present invention. Although the ammonia 55 and the methanol 56 are manufactured in the embodiment of FIG. 16, in this embodiment, as a chemical product manufacturing device, a device capable of manufacturing urea by the urea synthesis unit 61 from the obtained ammonia 55 is provided.

As illustrated in FIG. 17, according to the chemical product manufacturing device 40 of this embodiment, the ammonia 55 obtained in the ammonia synthesis unit 46 is further introduced into the urea synthesis unit 61 to manufacture urea in the chemical product manufacturing device 40 of FIG. 14.

According to the chemical product manufacturing device 40 that manufactures urea and methanol according to the present embodiment, it is possible to obtain the urea 62 using the ammonia 55 obtained in the ammonia synthesis unit 46 as the raw material, and the methanol 56 obtained in the methanol synthesis unit 47, and it is possible to simultaneously manufacture the urea 62 and the methanol 56 in parallel.

Thus, according to the chemical product manufacturing device 40 that manufactures urea and methanol, by providing the reforming device 10 of the first embodiment, similar to the chemical product manufacturing device 40 that manufactures ammonia according to the second embodiment, it is possible to improve the thermal efficiency when reforming the natural gas 21, and it is possible to suppress the occurrence of corrosion in the passage of the flue gas discharging line L12 in the course of processing the flue gas 22. Therefore, according to the chemical product manufacturing device 40 that manufactures urea, it is possible to stably produce the urea 62 and the methanol 56 and to improve their production efficiency.

[Manufacturing Example of Methanol]

Figure 18:
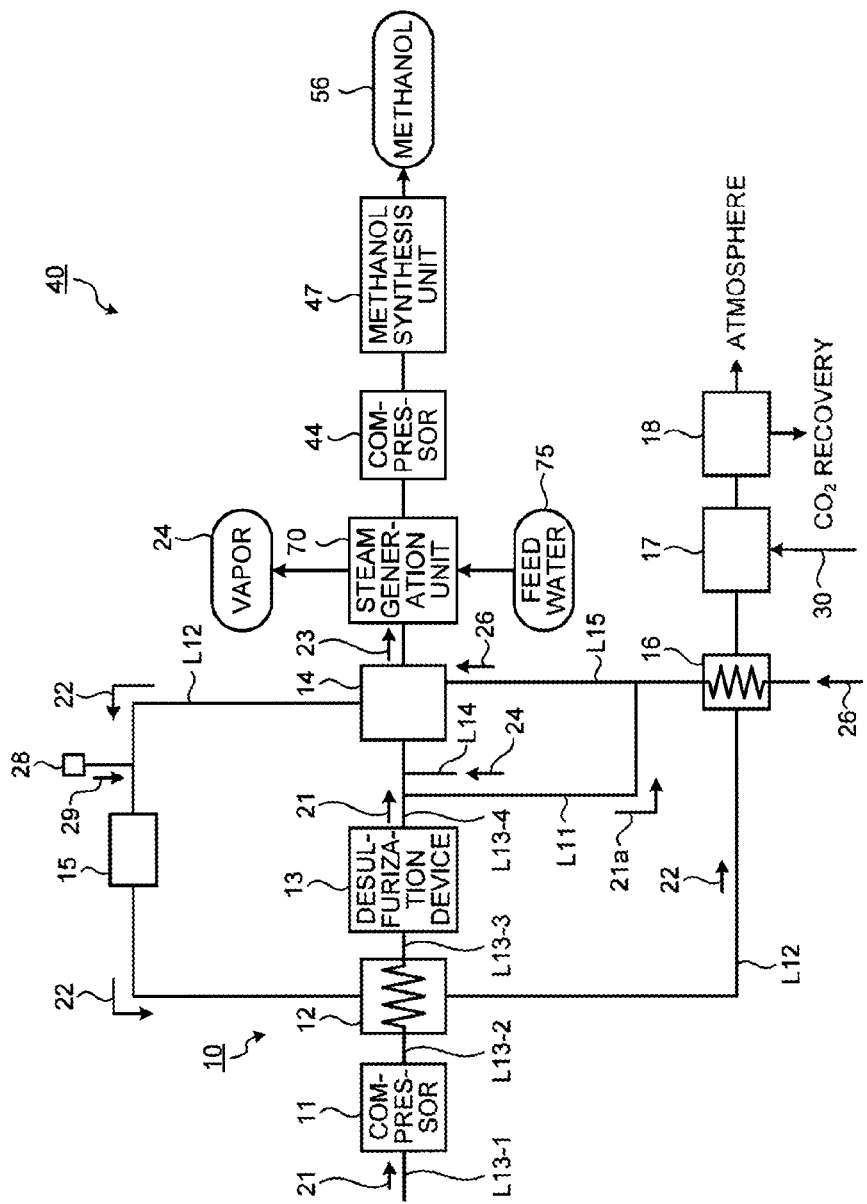
FIG. 18 is a schematic diagram of a chemical product manufacturing device equipped with another reforming device according to the second embodiment of the present invention.
Figure 19:
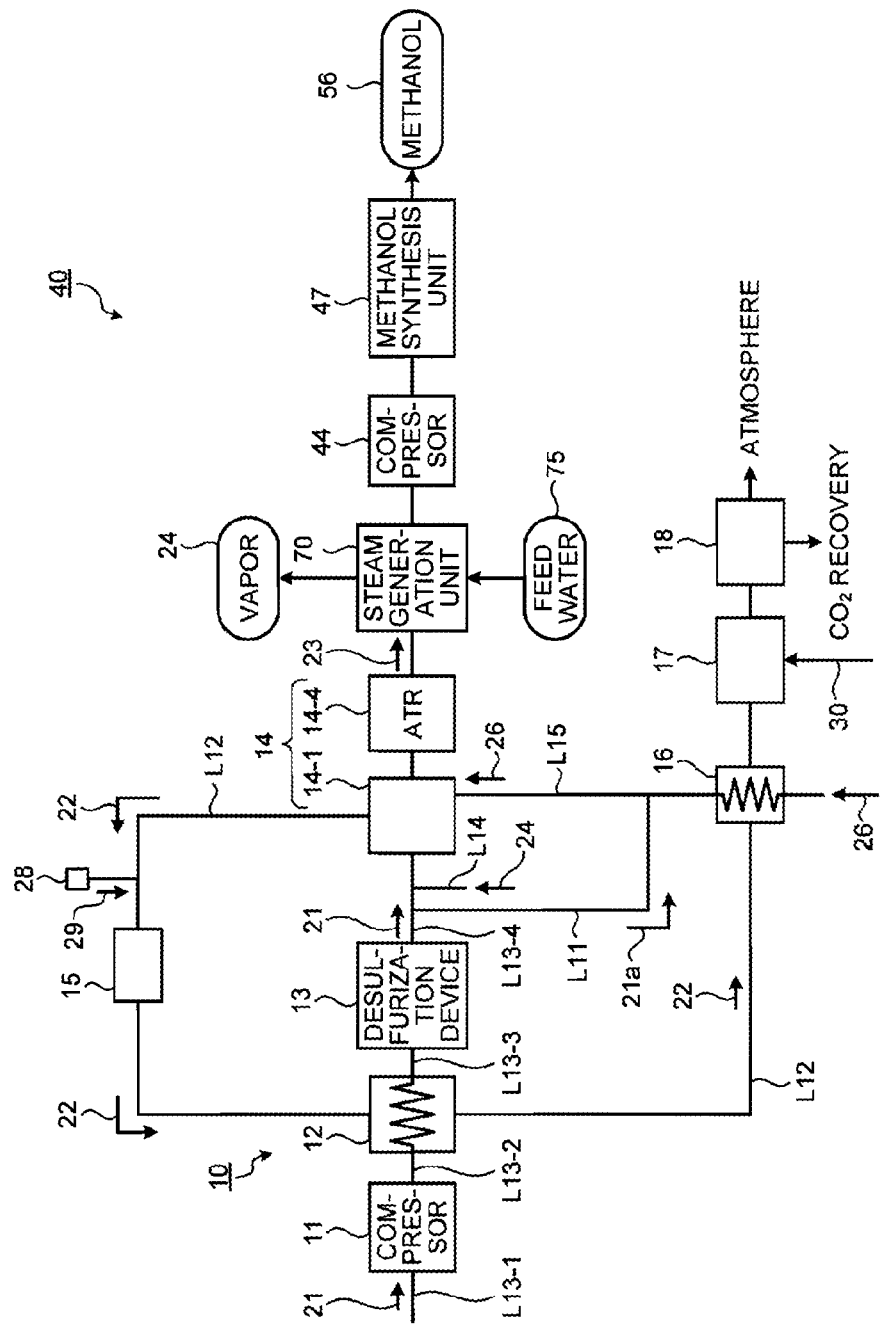
FIG. 19 is a schematic diagram of a chemical product manufacturing device equipped with another reforming device according to the second embodiment of the present invention.

FIGS. 18 and 19 are schematic diagrams of the chemical product manufacturing device equipped with the reforming device according to the second embodiment of the present invention. In the above-described embodiments, a device for manufacturing only methanol is provided as the chemical product manufacturing device.

As illustrated in FIG. 18, the chemical product manufacturing device 40 for manufacturing methanol has a reforming device 10, a steam generation unit 70, a compressor 44, and a methanol synthesis unit 47.

The chemical product manufacturing device 40 of the present embodiment is intended to synthesize the methanol 56, by using carbon dioxide and hydrogen in the reformed gas 23 obtained in the reforming device 10 as the raw material. It is possible to use the methanol synthesis unit 47 that has been generally used hitherto, and for example, a methanol synthesis device having a catalytic reactor is used.

Further, as illustrated in FIG. 19, the reformer 14 has a two-stage configuration, the first reformer 14-1 has the configuration of the reformer of FIG. 1, the second reformer 14-4 is used as an auto-thermal reforming furnace (ATR: Auto Thermal Reformer), and oxygen in place of air is supplied to the reformer to obtain a reformed gas 23 having a gas composition that is suitable for methanol synthesis.

In addition, in the above-described second embodiment, although the description has been given of a case where ammonia, methanol or urea is manufactured by alone or in co-production, the second embodiment is not limited thereto, and it can also be similarly applied to a case where ammonia or urea and other hydrocarbon are simultaneously manufactured in parallel.

Also, the reforming device 10 can also be similarly used in a hydrogen manufacturing system that manufactures hydrogen, and a system that manufactures liquid fuel of liquid hydrocarbon by the FT synthesis. Also, it may be manufactured by combining a plurality of these chemical products.

REFERENCE SIGNS LIST

10 REFORMING DEVICE
11 COMPRESSOR (FIRST COMPRESSION UNIT)
12 FIRST HEAT EXCHANGER (HEAT EXCHANGE UNIT)
13 DESULFURIZATION DEVICE (DESULFURIZATION UNIT)
14 REFORMER (REFORMING UNIT)
14A MAIN BODY
14B CATALYST REACTION TUBE
14C BURNER
14-1 FIRST REFORMER
14-2 SECOND REFORMER
14-3 PRE-REFORMER
15 DENITRIFICATION DEVICE (DENITRIFICATION UNIT)
16 SECOND HEAT EXCHANGER (HEAT EXCHANGE UNIT)
17 COOLING DEVICE
18 $CO_2$ RECOVERY DEVICE ($CO_2$ RECOVERY UNIT)
19 THIRD HEAT EXCHANGER (HEAT EXCHANGE UNIT)
20 FOURTH HEAT EXCHANGER (HEAT EXCHANGE UNIT)
21 NATURAL GAS
22 FLUE GAS
23 REFORMED GAS
24 VAPOR
26 COMBUSTION AIR
28 REDUCING AGENT INJECTOR
29 REDUCING AGENT
30 COOLING WATER
40 CHEMICAL PRODUCT MANUFACTURING DEVICE
41 CO SHIFT REACTION DEVICE (CO SHIFT REACTION UNIT)
42 CARBON DIOXIDE REMOVAL DEVICE (CARBONIC DIOXIDE REMOVAL UNIT)
43 METHANATION DEVICE (METHANATION UNIT)
44, 44-1, 44-2 COMPRESSOR
45 HYDROGEN SEPARATION DEVICE
46 AMMONIA SYNTHESIS UNIT
47 METHANOL SYNTHESIS UNIT
51 SHIFT GAS
52, 53 $CO_2$ REMOVAL GAS
55 AMMONIA
56 METHANOL
61 UREA SYNTHESIS UNIT
62 UREA
L11, L21 RAW MATERIAL GAS BRANCHING LINE
L12 FLUE GAS DISCHARGING LINE
L13-1 to L13-4 RAW MATERIAL GAS SUPPLY LINE
L14 VAPOR SUPPLY LINE
L15 AIR SUPPLY LINE
L31 CARBON DIOXIDE SUPPLY LINE
L32 HYDROGEN SUPPLY LINE
L33 CARBON DIOXIDE BRANCHING SUPPLY LINE

The invention claimed is:

1. A reforming device comprising:
a raw material gas supply line configured to supply a raw material gas containing hydrocarbon and sulfur;
a first compression unit configured to compress the raw material gas supplied through the raw material gas supply line;
a desulfurization unit configured to remove sulfur content contained in the compressed raw material gas;
a raw material gas branching line configured to extract a part of the compressed raw material gas from a downstream side of the desulfurization unit, and through which the part of the compressed raw material gas which has been desulfurized in the desulfurization unit is supplied;
a reforming unit including a burner, the reformer configured to reform the hydrocarbon in the raw material gas desulfurized in the desulfurization unit to either one or both of $H_2$ and CO or $H_2$ and $CO_2$ to generate a reformed gas containing either one or both of $H_2$ and CO or $H_2$ and $CO_2$ by combustion;
a flue gas discharging line configured to discharge a flue gas, which is generated by combustion in the reforming unit, from the reforming unit;
a first heat exchanger that is provided on a junction of the raw material gas supply line and the flue gas discharging line at a downstream side of the first compression unit, configured to heat-exchange the compressed raw material gas with the flue gas supplied through the flue gas discharging line as a heating medium;
a fourth heat exchanger that is provided on a junction of the raw material gas supply line and the raw material gas branching line between the first compression unit and the first heat exchanger, configured to heat-exchange the compressed raw material gas with the part of the raw material gas supplied through the raw material gas branching line;
a second heat exchanger that is provided on the flue gas discharging line at a downstream side of the first heat exchanger, configured to heat-exchange combustion air used for heating in the reforming unit with the flue gas which has been heat-exchanged in the first heat exchange unit;
a third heat exchanger that is provided on the flue gas discharging line between the first heat exchanger and the second heat exchanger, configured to heat-exchange feed water to be supplied to a steam generation unit with the flue gas;
wherein the raw material gas branching line is connected to the reforming unit to supply the part of the compressed raw material which has been desulfurized to the reforming unit as a combustion fuel for heating therein.

2. The reforming device according to claim 1, wherein the reforming unit has a first reforming unit configured to supply vapor to the raw material gas to primarily reform the hydrocarbon in the raw material gas to either one or both of $H_2$ and CO or $H_2$ and $CO_2$, and a second reforming unit configured to secondarily reform the hydrocarbon in the raw material gas after the primary reforming in the first reforming unit to either one or both of $H_2$ and CO or $H_2$ and $CO_2$ to be a reformed gas, using the combustion air and the compressed raw material gas supplied from the raw material gas branching line.

3. The reforming device according to claim 1, comprising any one or both of:

a denitrification unit that is provided between the reforming unit of the flue gas discharging line and the second heat exchanger, configured to remove NOx contained in the flue gas that is generated in the reforming unit; and a CO2 recovery unit that is provided on the downstream side of the second heat exchanger with respect to the flow direction of the flue gas of the flue gas discharging line, configured to remove CO2 contained in the flue gas.

4. A device for manufacturing chemical products comprising:

the reforming device according to claim 1; and a chemical product generation unit configured to manufacture chemical products using the reformed gas.

5. The device for manufacturing chemical products according to claim 4, wherein the chemical product generation unit is an ammonia synthesis unit that synthesizes ammonia using the reformed gas.

6. The device for manufacturing chemical products according to claim 4, wherein the chemical product generation unit is a urea synthesis unit that synthesizes urea using the reformed gas.

7. The device for manufacturing chemical products according to claim 4, wherein the chemical product generation unit is a methanol synthesis unit that synthesizes methanol using the reformed gas.

* * * * *